US009051583B2

(12) United States Patent
Mirkin et al.

(10) Patent No.: US 9,051,583 B2
(45) Date of Patent: Jun. 9, 2015

(54) MODIFIED SILICA SHELL PARTICLES, AND METHODS OF MAKING AND USING THE SAME

(71) Applicant: NORTHWESTERN UNIVERSITY, Evanston, IL (US)

(72) Inventors: Chad A. Mirkin, Wilmette, IL (US); Kaylie L. Young, Endicott, NY (US); Alexander Wesley Scott, Aldie, VA (US); Liangliang Hao, Evanston, IL (US); Sarah Mirkin, Wilmette, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 103 days.

(21) Appl. No.: 13/719,913

(22) Filed: Dec. 19, 2012

(65) Prior Publication Data

US 2013/0217124 A1  Aug. 22, 2013

Related U.S. Application Data

(60) Provisional application No. 61/577,419, filed on Dec. 19, 2011.

(51) Int. Cl.
| | | |
|---|---|---|
| *C12N 15/85* | (2006.01) | |
| *B82Y 5/00* | (2011.01) | |
| *C12N 15/87* | (2006.01) | |
| *C12N 5/071* | (2010.01) | |

(52) U.S. Cl.
CPC ........... *C12N 15/85* (2013.01); *Y10T 428/2991* (2015.01); *C12N 15/87* (2013.01)

(58) Field of Classification Search
USPC ........... 424/9.1, 94.1; 435/375, 6, 1; 977/702, 977/906, 920, 927
See application file for complete search history.

(56) References Cited

U.S. PATENT DOCUMENTS

| | | | |
|---|---|---|---|
| 4,489,055 A | 12/1984 | Couvreur et al. | |
| 5,472,881 A | 12/1995 | Beebe et al. | |
| 6,361,944 B1 | 3/2002 | Mirkin et al. | |
| 6,417,340 B1 | 7/2002 | Mirkin et al. | |
| 6,495,324 B1 | 12/2002 | Mirkin et al. | |
| 6,506,564 B1 | 1/2003 | Mirkin et al. | |
| 6,582,921 B2 | 6/2003 | Mirkin et al. | |
| 6,602,669 B2 | 8/2003 | Letsinger et al. | |
| 6,610,491 B2 | 8/2003 | Mirkin et al. | |
| 6,677,122 B2 | 1/2004 | Mirkin et al. | |
| 6,678,548 B1 | 1/2004 | Echauz et al. | |
| 6,682,895 B2 | 1/2004 | Mirkin et al. | |
| 6,709,825 B2 | 3/2004 | Mirkin et al. | |
| 6,720,147 B2 | 4/2004 | Mirkin et al. | |
| 6,720,411 B2 | 4/2004 | Mirkin et al. | |
| 6,750,016 B2 | 6/2004 | Mirkin et al. | |
| 6,759,199 B2 | 7/2004 | Mirkin et al. | |
| 6,767,702 B2 | 7/2004 | Mirkin et al. | |
| 6,773,884 B2 | 8/2004 | Mirkin et al. | |
| 6,777,186 B2 | 8/2004 | Mirkin et al. | |
| 6,812,334 B1 | 11/2004 | Mirkin et al. | |
| 6,818,753 B2 | 11/2004 | Mirkin et al. | |
| 6,827,979 B2 | 12/2004 | Mirkin et al. | |
| 6,828,432 B2 | 12/2004 | Mirkin et al. | |
| 6,861,221 B2 | 3/2005 | Mirkin et al. | |
| 6,878,814 B2 | 4/2005 | Mirkin et al. | |
| 6,974,669 B2 | 12/2005 | Mirkin et al. | |
| 7,323,309 B2 | 1/2008 | Mirkin et al. | |
| 2002/0172953 A1 | 11/2002 | Mirkin et al. | |
| 2003/0147966 A1 | 8/2003 | Franzen et al. | |
| 2010/0291707 A1 | 11/2010 | Mirkin et al. | |
| 2012/0267585 A1* | 10/2012 | Wang et al. | 252/645 |
| 2013/0089614 A1* | 4/2013 | Zhang et al. | 424/489 |

FOREIGN PATENT DOCUMENTS

| | | | | |
|---|---|---|---|---|
| WO | WO-98/04740 A1 | 2/1998 | | |
| WO | WO-00/62626 A1 | 10/2000 | | |
| WO | WO-01/51665 A2 | 7/2001 | | |
| WO | WO-01/73123 A2 | 10/2001 | | |
| WO | WO 2005111240 A2 * | 11/2005 | | C12Q 1/68 |
| WO | WO-2008/098248 A2 | 8/2008 | | |
| WO | WO-2008/151049 A2 | 12/2008 | | |
| WO | WO-2010/081019 A1 | 7/2010 | | |

OTHER PUBLICATIONS

Shi et al. 2007. Tailored Core-Shell-Shell Nanostructures: Sandwiching Gold Nanoparticles between Silica Cores and Tunable Silica Shell. Langmuir, vol. 23, pp. 9455-9462.*
Liu et al. 2010. Silica-Coated Metal Nanoparticles. Chemistry Asian Journal. vol. 2010, 5, pp. 36-45.*
Fine particles part II: Formation mechanisms and applications, MRS Bulletin: A Publication of the Materials Research Society, pp. 16-47 (Jan. 1990)
Ahmadi et al., Shape controlled synthesis of colloidal platinum nanoparticles, Science, 272:1924-6 (1996).
Allara et al., The study of gas-solid interaction of acetic acid with a cuprous oxide surface using reflection-absorption spectroscopy, J. Colloid Interface Sci., 49:410-421 (1974).
Allara et al., Spontaneously organized molecular assemblies. 1. Formation, dynamics and physical properties of n-Alkanoic acid adsorbed from solution on an oxidized aluminum surface, Langmuir, 1: 45-52 (1985).
Altschul et al., Basic local alignment search tool, J. Mol. Biol. 215:403-10 (1990).
Bahnemann, Mechanism of organic transformations on semiconductor particles, In: Pelizzetti et al. (eds.), Photochemical Conversion and Storage of Solar Engery, Proceedings of the Eighth International Conference on Photochemical Conversion and Storage of Solar Energy, Palermo, Italy (Jul. 15-20, 1990).

(Continued)

*Primary Examiner* — Jon P Weber
*Assistant Examiner* — Kailash C Srivastava
(74) *Attorney, Agent, or Firm* — Marshall, Gerstein & Borun LLP

(57) ABSTRACT

Provided herein are silica shell particles modified on their surface with biomolecules, methods of making these particles, and methods of using these particles, e.g., in transfection methods, methods of inhibiting gene expression, and methods of delivering a therapeutic.

18 Claims, 3 Drawing Sheets

(56) References Cited

OTHER PUBLICATIONS

Banholzer et al., Abnormally Large Plasmonic Shifts in Silica-Protected Gold Triangular Nanoprisms, J. Phys. Chem. C, 114:7521-6 (2010).
Barnes et al., Reproducible Comet Assay of Amorphous Silica Nanoparticles Detects No Genotoxicity, Nano Lett., 8:3069-74 (2008).
Baskin et al., Copper-free click chemistry for dynamic in vivo imaging, Proc. Natl. Acad. Sci., USA, 104(43):16793-7 (2007).
Bhabra et al., Nanoparticles can cause DNA damage across a cellular barrier. Nat. Naonotechnol., 4(12):876-83 (2009).
Burwell Modified silica gels as adsorbents and catalysts, Chem. Technol., 4, 370-7 (1974).
Chompoosor et al., The role of surface functionality on acute cytotoxicity, ROS generation and DNA damage by cationic gold nanoparticles. Small, 6(20):2246-9 (2010).
Curtis et al., A morphology selective copper organosol, Angew. Chem. Int. Ed. Engl., 27:1530 (1988).
Cutler et al., Polyvalent nucleic acid nanostructures, J. Am. Chem. Soc., 133 (24):9254-7 (2011).
Cutler et al., Spherical nucleic acids, J. Am. Chem. Soc., 134(3):1376-91 (2012).
Dokka et al., Oxygen radical-mediated pulmonary toxicity induced by some cationic liposomes, Pharm. Res., 17(5):521-5 (2000).
Eltekova et al., Adsorption of aromatic compounds from solutions on titanium dioxide and silica, Langmuir, 3:951-957 (1987).
Enustun et al., Coagulation of colloidal gold, J. Am. Chem. Soc., 85:3317-28 (1963).
Fattal et al., Biodegradable polyalkylcyanoacrylate nanoparticles for the delivery of oligonucleotides, J. Control. Release, 53:137-43 (1998).
Frens et al., Controlled nucleation for the regulation of the particle size in monodisperse gold suspensions, Nature Physical Science, 241:20-2 (1973).
Giljohann et al., Oligonucleotide loading determines cellular uptake of DNA-modified gold nanoparticles, Nano Lett., 7(12):3818-21 (2007).
Grabar et al., Preparation and characterization of Au colloid monolayers, Anal Chem, 67 : 735-743 (1995).
Hayashi, Ultrafine particles, Physics Today, 44-60 (1987).
Hayashi, Ultrafine particles, Vac. Sci. Technol. A, 5:1375-84 (1987).
Hayat (ed.), Colloidal Gold: Principles, Methods, and Applications, San Diego, CA: Academic Press (1991).
Henglein et al., Absorption spectrum and some chemicl reactions of colloidal platinum in aqueous solution. J. Phys. Chem., 99:14129-36 (1995).
Henglein, Small-particle research: physiochemical properties of extremely small colloidal metal and semiconductor particles, Chem. Rev., 89:1861-73 (1989).
Hermanson, Bioconjugate Techniques, 2nd ed., San Diego, Calif.: Academic Press (2008).
Hickman et al., Combining spontaneous molecular assembly with microfabrication to pattern surfaces: selective binding of isonitriles to platinum microwires and characterization by electrochemistry and surface spectroscopy, J. Am. Chem. Soc., 111: 7271-7272 (1989).
Hubbard, Electrochemistry of well-defined surfaces, Acc. Chem. Res., 13:177-184 (1980).
Hurst et al., Maximizing DNA loading on a range of gold nanoparticle sizes, Anal. Chem., 78:8313-8318 (2006).
Iler, The Chemistry of Silica, Chapter 6, New York: Wiley (1979).
Jin et al., Preparation of End-Tethered DNA Monolayers on Siliceous Surfaces Using Herterobifunctional Cross-Linkers, Langmuir, 19:6968-75 (2003).
Jin et al., What controls the Melting Properties of DNA-Linked Gold Nanoparticle Assemblies?, J. Am. Chem. Soc., 125(6):1643-54 (2003).
Kelly et al., The Optical Properties of Metal Nanoparticles: The Influence of Size, Shape, and Dielectric Environment, J. Phys. Chem. B, 107(3):668-77 (2003).
Kolb et al., Click chemistry: diverse chemical function from a few good reactions, Angew. Chem. Int. Ed., 40:2004-21 (2001).
Kukowska-Latallo et al., Efficient transfer of genetic material into mammalian cells using Starburst polyamidoamine dendrimers, Proc. Natl. Acad. Sci. USA, 93:4897-902 (1996).
Lee et al., Adsorption of ordered zirconium phosphonate multilayer films on silicon and gold surfaces, J. Phys. Chem., 92 : 2597-601 (1988).
Lee et al. Chip-based scanometric detection of mercuric ion using DNA-functionalized gold nanoparticles, Anal. Chem., 80:6805-8 (2008).
Letsinger et al., Use of a steroid cyclic disulfide anchor in construction gold nanoparticle-oligonucleotide conjugates, Bioconjug. Chem., 11(2):289-91 (2000).
Lewis, Controlled release of bioactive agents from lactide/glycolide polymer, pp. 1-241, In: Chasin et al. (eds.), Biodegradable Polymers as Drug Delivery Systems, New York: Marcel Dekker (1990).
Liu et al., New poly(d-glucaramidoamine)s induce DNA nanoparticle formation and efficient gene delivery into mammalian cells, J. Am. Chem. Soc. 126:7422-3 (2004).
Liu et al., Adv. Funct. Mater., 15:961-7 (2005).
Liu et al., ARDB—Antibiotic Resistance Genes Database, Nucleic Acids Res., 37 (Database Issue):D443-7 (2009).
Lu et al., Synthesis and Self Assembly of Au@SiO2 Core?Shell Colloids, Nano Lett., 2:785-8 (2002).
Lv et al., Toxicity of cationic lipids and cationic polymers in gene delivery, J. Control. Release, 114(1): 100-9 (2006).
Lytton-Jean et al., A therodynamic investigation into the binding properties of DNA functionalized gold nanoparticle probes and molecular fluorophore probes, J. Am. Chem. Soc., 127:12754-5 (2005).
Maoz et al., Penetration-controlled reactions in organized monolayer assemblies, 1. Aqueous permanganate interaction with monolayer and multilayer films of long-chain surfactants, Langmuir, 3:1034-44 (1987).
Maoz et al., Penetration-controlled reactions in organized monolayers assemblies, 2. Aqueous permanganate interaction with self-assembling monolayers of long-chain surfactants, Langmuir, 3:1045-51 (1987).
Marinakos et al., Gold nanoparticles as templates for the synthesis of hollow nanometer-sized conductive polymer capsules, Adv. Mater, 11:34-37 (1999).
Marinakos et al., Template synthesis of one-dimensional Au, Au-poly(pyrrole), and poly(pyrrole) nanoparticle arrays, Chem Mater, 10:1214-19 (1998).
Marinakos et al., Gold Particles as Templates for the Synthesis of Hollow Polymer Capsules. Control of Capsule Dimensions and Guest Encapsulation, J. Am. Chem. Soc., 121:8518-22 (1999).
Massart, Preparation of aqueous magnetic liquids in alkaline and acidic media, IEEE Transactions on Magnetics, 17, 1247-8 (1981).
Massich et al., Regulating immune response using polyvalent nucleic acid-gold nanoparticle conjugates, Mol. Pharm., 6(6):1934-40 (2009).
Matteucci et al., Synthesis of deoxyoligonucleotides on a polymer support, J Am Chem Soc, 103, 3185-3191 (1981).
Mine et al., Direct coating of gold nanoparticles with silica by a seeded polymerization technique, J. Colloid Interface Sci., 264(2):385-90 (2003).
Nel et al., Toxic potential of materials at the nanolevel, Science, 311 (5761):622-7 (2006).
Nuzzo et al., Spontaneously organized molecular assemblies. 3. Preparation and properties of solution adsorbed monolayers of organic disulfides on gold surfaces, J Am Chem Soc, 109:2358-2368 (1987).
Olshavsky et al., Organometallic synthesis of GaAs crystallites exhibiting quantum confinement, J. Am. Chem. Soc., 112:9438-9 (1990).
Park et al., Biodegradable luminescent porous silicon nanoparticles in vivo applications, Nat. Mater., 8(4):331-6 (2009).
Patel et al., Scavenger receptors mediate cellular uptake of polyvalent oligonucleotide-functionalized gold nanoparticles, Bioconjug. Chem., 21( 12):2250-6 (2010).

(56) References Cited

OTHER PUBLICATIONS

Rosi et al., Oligonucleotide-modified gold nanoparticles for intracellular gene regulation, Science, 312:1027-30 (2006).

Schmid et al., Siloxane Polymers for High Resolution, High Accuracy Soft Lithography, Macromolecules, 33:3042-9 (2000).

Seferos et al., Nano-flares: probes for transfection and mRNA detection in living cells, J. Am. Chem. Soc., 129:15470-7 (2007).

Seferos et al., Polyvalent DNA nanoparticle conjugates stablize nucleic acids, Nano Lett., 9(1):308-11 (2009).

Soenen et al. Addressing the problem of cationic lipid-mediated toxicity: the magnetoliposome model, Biomaterials, 30(22):3691-701 (2009).

Sokolova et al., Inorganic nanoparticles as carriers of nucleic acids into cells, Angew. Chem. Int. Ed, Engl., 47(8):1382-95 (2008).

Soriaga et al., Determination of the orientation of aromatic molecules adsorbed on platinum electrodes. The effect of solute concentration, J Am Chem Soc, 104:3937-45 (1982).

Timmons et al., Investigation of fatty acid monolayers on metals by contact potential measurements, J Phys Chem, 69:984-990 (1965).

Tondelli et al., Highly efficient cellular uptake of c-myb antisense oligonucleotides through specifically designed polymeric nanospheres, Nucleic Acids Res., 26:5425-31 (1998).

Ushida et al., GaAs nanocrystals prepared in quinoline, J. Phys. Chem., 95:5382-4 (1991).

Wang et al., Nanometer-sized semiconductor clusters: materials synthesis, quantum size effects and photophysical properties, J. Phys. Chem. 95:525-32 (1991).

Weller, Colloidal semiconductor Q-particles: chemistry in the transition region between solid state and molecules, Angew. Chem. Int. Ed. Engl., 32:41-53 (1993).

Wong et al., Revisiting the Stöber method: Inhomogeneity in silica shells, J. Am. Chem. Soc., 133(30):11422-5 (2011).

Xue et al., Self-assembled monolayer mediated silica coating of silver triangular nanoprisms, Adv. Mater., 19:4071-4 (2007).

Yamada et al., Preparation of colloidal Mesoporous Silica Nanoparticles with Different Diameters and Their Unique Degradation Behavior in Static Aqueous Systems, Chem. Mater., 24:1462-71 (2012).

Zhang et al., PowerBLAST: A new network BLAST application for interactive or automated sequence analysis and annotation, Genome Res., 7:649-56 (1997).

* cited by examiner

SEQUENCE LISTING

```
<160> NUMBER OF SEQ ID NOS: 9

<210> SEQ ID NO 1
<211> LENGTH: 30
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (30)..(30)
<223> OTHER INFORMATION: 3' (C3H6)-thiol

<400> SEQUENCE: 1
cggacacgct gaacttgtgg aaaaaaaaaa                                    30

<210> SEQ ID NO 2
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (25)..(25)
<223> OTHER INFORMATION: 3' (C3H6)-thiol

<400> SEQUENCE: 2
atccttatca atattaaaaa aaaaa                                         25

<210> SEQ ID NO 3
<211> LENGTH: 30
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' Cy5 label
<220> FEATURE:
<221> NAME/KEY: misc_feature
<222> LOCATION: (30)..(30)
<223> OTHER INFORMATION: 3' (C3H6)-thiol

<400> SEQUENCE: 3
```
cggacacgct gaacttgtgg aaaaaaaaaa                                          30

<210> SEQ ID NO 4
<211> LENGTH: 28
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (28)..(28)
<223> OTHER INFORMATION: 3' (C3H6)-thiol

<400> SEQUENCE: 4
gaataattat aagcagaaaa aaaaaaaa                                            28

<210> SEQ ID NO 5
<211> LENGTH: 60
<212> TYPE: DNA
<213> ORGANISM: Artificial Sequence
<220> FEATURE:
<223> OTHER INFORMATION: Synthetic linker

<400> SEQUENCE: 5
ttctgcttat aaattcttat tttttttttt tactgagcag cactgatttt tttttttta        60

<210> SEQ ID NO 6
<211> LENGTH: 21
<212> TYPE: DNA
<213> ORGANISM: Artificial Sequence
<220> FEATURE:
<223> OTHER INFORMATION: Synthetic primer

<400> SEQUENCE: 6
ccacatgaag cagcacgact t                                                  21

<210> SEQ ID NO 7
<211> LENGTH: 18
<212> TYPE: DNA
<213> ORGANISM: Artificial Sequence
<220> FEATURE:
<223> OTHER INFORMATION: Synthetic primer

<400> SEQUENCE: 7
ggtgcgctcc tggacgta                                                      18

<210> SEQ ID NO 8
<211> LENGTH: 18
<212> TYPE: DNA
<213> ORGANISM: Artificial Sequence
<220> FEATURE:
<223> OTHER INFORMATION: Synthetic primer

<400> SEQUENCE: 8
cacgtgggct ccagcatt                                                      18

<210> SEQ ID NO 9
<211> LENGTH: 22
<212> TYPE: DNA
<213> ORGANISM: Artificial Sequence
<220> FEATURE:
<223> OTHER INFORMATION: Synthetic primer

<400> SEQUENCE: 9
tcaccagtca tttctgcctt tg                                                 22

MODIFIED SILICA SHELL PARTICLES, AND METHODS OF MAKING AND USING THE SAME

STATEMENT OF GOVERNMENT INTEREST

This invention was made with government support under Grant Number DMR-0520513, awarded by the National Science Foundation; Grant Number FA9550-11-1-0275, awarded by Air Force Office of Scientific Research; and Grant Number U54CA151880, awarded by the National Institute of Health/National Cancer Institute. The government has certain rights in the invention.

CROSS-REFERENCE TO RELATED APPLICATIONS

The benefit of U.S. Provisional Application No. 61/577,419, filed Dec. 19, 2011, is claimed, the disclosure of which is incorporated by reference in its entirety.

INCORPORATION BY REFERENCE OF MATERIAL SUBMITTED ELECTRONICALLY

This application contains, as a separate pat of disclosure, a Sequence Listing in computer-readable form (filename: 2011_166_SeqListing.txt; 2,396 byte—ASCII text file) which is incorporated by reference in its entirety.

BACKGROUND

Recent work has shown that spherical nucleic acids (SNAs), structures consisting of linear nucleic acids that are highly oriented and densely packed on the surface of a spherical nanoparticle (NP), exhibit the ability to efficiently enter cells without a transfection agent. (1,2) This is in contrast to free linear nucleic acids, which generally require a cationic moiety to neutralize their negative charge to pass through the cellular membrane. (3) However, these cationic lipids and polymers often display cytotoxic effects at high concentrations and the inability to be degraded biologically. (4-6) SNA-NP conjugates thus provide a unique platform for internalizing large quantities of nucleic acids into cells under mild conditions that can subsequently be used for intracellular detection (7) and gene regulation. (1) Thus far, it has been shown that scavenger receptors mediate the cellular entry of SNAs (8) and cellular uptake is dependent on the density of nucleic acids on the nanoparticle surface. (9) Furthermore, SNA-NP conjugates have a unique set of properties that are advantageous for intracellular applications, including high binding coefficients for DNA that is complementary and RNA, (10) nuclease resistance, (11) and minimal immune response. (12) With respect to cellular internalization and activity, these observations are all based upon the hypothesis that the unique properties of the SNA architecture stem from the oligonucleotide shell and the density and orientation of the nucleic acids that comprise it as opposed to the nanoparticle core. A synthetic route has also been demonstrated for making hollow SNAs by cross-linking oligonucleotides on the surface of gold nanoparticles and subsequently dissolving the gold particle template. Consistent with our hypothesis, these structures are capable of cellular internalization and gene regulation via antisense and RNAi pathways. (13) The hollow structures are attractive, especially if one is concerned about the long-term toxicity of the gold nanoparticle core. (14-16) The disadvantage of the approach is that specialty oligonucleotides capable of cross-linking are required, and at present, they are prohibitively expensive. These observations pose the challenge of identifying other chemical routes to hollow SNA structures that possess similar properties to those derived from gold particles and perhaps offer even greater capabilities.

SUMMARY

Provided herein are silica shell particles, methods of making silica shell particles, and methods of using the same. Thus, provided is a method comprising admixing a nanoparticle and a silica reagent to form a silica shell nanoparticle; admixing the silica shell nanoparticle and a biomolecule to attach the biomolecule to at least a portion of the silica shell nanoparticle surface; and at least partially removing the nanoparticle to form a biomolecule-surface modified silica shell particle. The method can optionally further comprise recovering the removed nanoparticle (e.g., via collection after dissolution of the nanoparticle material). In various cases, the silica shell particle can have a diameter of about 30 to about 500 nm, about 40 nm to about 200 nm, or about 40 nm to about 100 nm.

The nanoparticle can be metallic, or can be a colloidal material. In some cases, the nanoparticle is a gold nanoparticle, a silver nanoparticle, a platinum nanoparticle, an aluminum nanoparticle, a palladium nanoparticle, a copper nanoparticle, a cobalt nanoparticle, an indium nanoparticle, or a nickel nanoparticle. The nanoparticle can have a diameter of about 5 nm to about 500 nm, or about 10 nm to about 250 nm, or about 10 nm to about 100 nm.

In some cases, the nanoparticle is completely removed to leave a silica shell hollow particle. In some cases, the removing agent comprises iodine, cyanide, or aqua regia. In some specific cases, the nanoparticle comprises gold and the removing agent comprises iodine.

The silica reagent can be a silicate, such as, for example, tetraethyl orthosilicate (TEOS). The silica shell can have a thickness of at least 10 nm and/or 250 nm or less. In some cases, the thickness is about 20 nm to about 200 nm. In some cases, the silica shell particle can be activated to introduce a reactive moiety compatible with the biomolecule to be attached, for example a thiol reactive moiety. In some specific cases, the reactive moiety comprises a maleimide.

The biomolecule can be a polynucleotide, peptide, polypeptide, phospholipid, oligosaccharide, small molecule, therapeutic agent, contrast agent or mixtures thereof. The biomolecule can comprise a thiol at one end. The biomolecule can have a density on the surface of the silica shell particle of at least 50 molecules per nanoparticle, 55 to 80 molecules per nanoparticle, at least 2 pmol/cm$^2$, at least 50 pmol/cm$^2$, or about 100 pmol/cm$^2$. In some cases, the biomolecule comprises a polynucleotide.

In various cases, the silica shell particle can be mixed with a therapeutic agent to form a payload particle, e.g., where the therapeutic agent is within the core of the particle where the removed or partially removed nanoparticle material was. The therapeutic agent can be, e.g., a protein, a peptide, an antibody, an oligonuceltoide, a polynucleotide, or a drug.

Further provided herein are methods of inhibiting expression of a gene product encoded by a target polynucleotide comprising contacting the target polynucleotide with a silica shell particle as disclosed herein under conditions sufficient to inhibit expression of the gene product, wherein the at least a portion of the silica shell particle surface is modified with a biomolecule, and said biomolecule comprises a oligonucleotide. In some cases, the contacting is in vivo. In such cases, the contacting can comprise administering the silica shell particle to a subject in need thereof. In other cases, the contacting is in vitro. In various cases, gene expression is inhibited by at least about 5%.

Further provided herein are methods of contacting a cell with a silica shell particle as disclosed herein under conditions to transfect the cell with the silica shell particle In some cases, the contacting is in vivo. In such cases, the contacting can comprise administering the silica shell particle to a subject in need thereof. In other cases, the contacting is in vitro.

DETAILED DESCRIPTION

Figure 1:
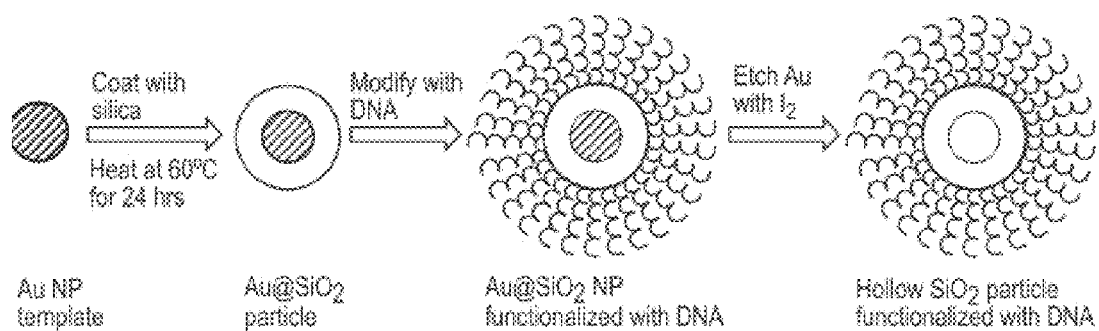
FIG. 1. Synthesis of DNA functionalized hollow $SiO_2$ particles using gold nanoparticles as sacrificial templates.

Reported herein is a new class of core-free SNA conjugate comprising a biocompatible porous silica shell. By using a silica-coated nanoparticle as a template, one can easily functionalize it with biomolecules, such as nucleic acids, using a wide variety of coupling strategies and relatively simple and readily available coupling molecules. The silica shell acts as a cross-linked scaffold to assemble oriented biomolecules (e.g, oligonucleotides) with a porous architecture that allows one to chemically dissolve the nanoparticle core. The hollow silica SNAs maintain the unique properties of the SNA nanoparticle conjugates (2,7-13,17) and exhibit the ability to be internalized by cells without a transfection agent and efficiently knock down a target mRNA sequence. Moreover, silica is an attractive material from a biological perspective since it is known to degrade into bioinert silicic acid under physiological conditions. (18) Previous studies of porous silica nanoparticles have shown a degradation rate of approximately 15% per day in a cellular environment. (19) In principle, these new SNA conjugates should degrade over time and release the biomolecule attached, e.g., active oligonucleotides.

As used herein, the term "silica shell particle" refers to a particle which comprises a silica shell modified on at least a portion of its surface with a biomolecule and having at least a portion of the nanoparticle removed. In some cases, the nanoparticle is substantially removed to provide a hollow inner core surrounded by a biomolecule-modified silica shell. When referring to a "nanoparticle" below, it is meant to refer to the initial templating particle on which the silica shell is deposited and which is then removed or at least partially removed.

The silica shell particle can further include a therapeutic agent that is incorporated into its hollow (or at least partially hollow) core. Such compositions are referred to herein as "payload particles."

Biomolecules

A biomolecule as used herein includes without limitation a polynucleotide, peptide, polypeptide, phospholipid, oligosaccharide, small molecule, therapeutic agent, contrast agent and mixtures thereof. In some cases, the biomolecule is further modified with, e.g., an antibody.

The biomolecule is attached to the silica shell surface via a covalent or noncovalent interaction. Exemplary noncovalent interactions include ionic and van der Waals interactions. Covalent interactions contemplated are bonds formed from a functional group on the biomolecule and a compatible functional group on the silica shell surface. Suitable choice of the functional groups of the biomolecule and silica shell surface are within the skill of the ordinarily skilled artisan.

The silica shell, the biomolecule, or both are functionalized in order to attach the biomolecule to the silica shell. Such methods are known in the art. For instance, oligonucleotides functionalized with a alkanethiols at their 3'-termini or 5'-termini readily attach to a silica shell that has been modified with a maleimide group, e.g., by derivatization with an aminoalkylsilane ((aminopropyl)triethoxysilane) and subsequent reaction with p-maleimidophenyl isocyanate. After derivatization of the silica shell with an aminoalkylsilane, the amino group can be used to covalently attach a biomolecule having other nucleophilic moieties (e.g., carboxylic acid, activated esters) or reacted via a reductive amination to attach the biomolecule. The biomolecule can also be attached via click chemistry, where one of the silica shell surface or the biomolecule is modified to include an alkyne moiety and the other to include an azide.

Other functional groups for attaching biomolecules to solid surfaces include phosphorothioate groups (see, e.g., U.S. Pat. No. 5,472,881 for the binding of oligonucleotide-phosphorothioates to gold surfaces), substituted alkylsiloxanes (see, e.g. Burwell, 1974, *Chemical Technology*, 4: 370-377 and Matteucci and Caruthers, 1981, *J. Am. Chem. Soc.*, 103: 3185-3191 for binding of oligonucleotides to silica and glass surfaces, and Grabar et al., 1995, *Anal. Chem.*, 67: 735-743 for binding of aminoalkylsiloxanes and for similar binding of mercaptoaklylsiloxanes). Oligonucleotides terminated with a 5' thionucleoside or a 3' thionucleoside may also be used for attaching oligonucleotides to solid surfaces. The following references describe other methods which may be employed to attach oligonucleotides to nanoparticles: Nuzzo et al., 1987, *J. Am. Chem. Soc.*, 109: 2358 (disulfides on gold); Allara and Nuzzo, 1985, *Langmuir*, 1: 45 (carboxylic acids on aluminum); Allara and Tompkins, 1974, *J. Colloid Interface Sci.*, 49: 410-421 (carboxylic acids on copper); Iler, The Chemistry Of Silica, Chapter 6, (Wiley 1979) (carboxylic acids on silica); Timmons and Zisman, 1965, *J. Phys. Chem.*, 69: 984-990 (carboxylic acids on platinum); Soriaga and Hubbard, 1982, *J. Am. Chem. Soc.*, 104: 3937 (aromatic ring compounds on platinum); Hubbard, 1980, *Acc. Chem. Res.*, 13: 177 (sulfolanes, sulfoxides and other functionalized solvents on platinum); Hickman et al., 1989, *J. Am. Chem. Soc.*, 111: 7271 (isonitriles on platinum); Maoz and Sagiv, 1987, *Langmuir*, 3: 1045 (silanes on silica); Maoz and Sagiv, 1987, *Langmuir*, 3: 1034 (silanes on silica); Wasserman et al., 1989, *Langmuir*, 5: 1074 (silanes on silica); Eltekova and Eltekov, 1987, *Langmuir*, 3: 951 (aromatic carboxylic acids, aldehydes, alcohols and methoxy groups on titanium dioxide and silica); Lec et al., 1988, *J. Phys. Chem.*, 92: 2597 (rigid phosphates on metals). Additionally, any suitable method for attaching oligonucleotides onto the nanoparticle surface may be used. A particularly preferred method for attaching oligonucleotides onto a surface is based on an aging process described in U.S. application Ser. No. 09/344,667, filed Jun. 25, 1999; Ser. No. 09/603,830, filed Jun. 26, 2000; Ser. No. 09/760,500, filed Jan. 12, 2001; Ser. No. 09/820,279, filed Mar. 28, 2001; Ser. No. 09/927,777, filed Aug. 10, 2001; and in International application nos. PCT/US97/12783, filed Jul. 21, 1997; PCT/US00/17507, filed Jun. 26, 2000; PCT/US01/01190, filed Jan. 12, 2001; PCT/US01/10071, filed Mar. 28, 2001, the disclosures which are incorporated by reference in their entirety. The aging process provides nanoparticle-oligonucleotide conjugates with unexpected enhanced stability and selectivity. The method comprises providing oligonucleotides preferably having covalently bound thereto a moiety comprising a functional group which can bind to the nanoparticles. The moieties and functional groups are those that allow for binding (i.e., by chemisorption or covalent bonding) of the oligonucleotides to nanoparticles. For instance, oligonucleotides having an alkanethiol, an alkanedisulfide or a cyclic disulfide covalently bound to their 5' or 3' ends can be used to bind the oligonucleotides to a variety of nanoparticles, including gold nanoparticles.

Silica shell particles as provided herein have a density of the biomolecules on the surface of the silica shell particle that is, in various aspects, sufficient to result in cooperative behavior between silica shell particles and between biomolecules on a single silica shell particle. In another aspect, the cooperative behavior between the silica shell particles increases the resistance of the biomolecule to degradation, and provides a sharp melting transition relative to biomolecules that are not part of a silica shell particle. In one aspect, the uptake of silica shell particles by a cell is influenced by the density of polynucleotides associated with the silica shell particle. As described in PCT/US2008/65366, incorporated herein by reference in its entirety, a higher density of polynucleotides on the surface of a polynucleotide functionalized nanoparticle is associated with an increased uptake of nanoparticles by a cell. This aspect is likewise contemplated to be a property of silica shell particles, wherein a higher density of biomolecules that make up a silica shell particle is associated with an increased uptake of a silica shell particle by a cell.

A surface density adequate to make the silica shell particles stable and the conditions necessary to obtain it for a desired combination of silica shell particles and biomolecules can be determined empirically. Broadly, the smaller the biomolecule and/or non-biomolecule that is used, the higher the surface density of that biomolecule and/or non-biomolecule can be. Generally, a surface density of at least 2 pmol/cm$^2$ will be adequate to provide stable silica shell particle-compositions. In some aspects, the surface density is at least 15 pmol/cm$^2$. Methods are also provided wherein the biomolecule is present in a silica shell particle at a surface density of at least 2 pmol/cm$^2$, at least 3 pmol/cm$^2$, at least 4 pmol/cm$^2$, at least 5 pmol/cm$^2$, at least 6 pmol/cm$^2$, at least 7 pmol/cm$^2$, at least 8 pmol/cm$^2$, at least 9 pmol/cm$^2$, at least 10 pmol/cm$^2$, at least about 15 pmol/cm$^2$, at least about 20 pmol/cm$^2$, at least about 25 pmol/cm$^2$, at least about 30 pmol/cm$^2$, at least about 35 pmol/cm$^2$, at least about 40 pmol/cm$^2$, at least about 45 pmol/cm$^2$, at least about 50 pmol/cm$^2$, at least about 55 pmol/cm$^2$, at least about 60 pmol/cm$^2$, at least about 65 pmol/cm$^2$, at least about 70 pmol/cm$^2$, at least about 75 pmol/cm$^2$, at least about 80 pmol/cm$^2$, at least about 85 pmol/cm$^2$, at least about 90 pmol/cm$^2$, at least about 95 pmol/cm$^2$, at least about 100 pmol/cm$^2$, at least about 125 pmol/cm$^2$, at least about 150 pmol/cm$^2$, at least about 175 pmol/cm$^2$, at least about 200 pmol/cm$^2$, at least about 250 pmol/cm$^2$, at least about 300 pmol/cm$^2$, at least about 350 pmol/cm$^2$, at least about 400 pmol/cm$^2$, at least about 450 pmol/cm$^2$, at least about 500 pmol/cm$^2$, at least about 550 pmol/cm$^2$, at least about 600 pmol/cm$^2$, at least about 650 pmol/cm$^2$, at least about 700 pmol/cm$^2$, at least about 750 pmol/cm$^2$, at least about 800 pmol/cm$^2$, at least about 850 pmol/cm$^2$, at least about 900 pmol/cm$^2$, at least about 950 pmol/cm$^2$, at least about 1000 pmol/cm$^2$ or more.

It is contemplated that the density of polynucleotides in a silica shell particle modulates specific biomolecule and/or non-biomolecule interactions with the polynucleotide on the surface and/or with the silica shell particle itself. Under various conditions, some polypeptides may be prohibited from interacting with polynucleotides that are part of a silica shell particle based on steric hindrance caused by the density of polynucleotides. In aspects where interaction of polynucleotides with a biomolecule and/or non-biomolecule that are otherwise precluded by steric hindrance is desirable, the density of polynucleotides in the silica shell particle is decreased to allow the biomolecule and/or non-biomolecule to interact with the polynucleotide.

Silica shell particles of larger diameter are, in some aspects, contemplated to be templated with a greater number of polynucleotides [Hurst et al., Analytical Chemistry 78(24): 8313-8318 (2006)] during silica shell particle production. In some aspects, therefore, the number of polynucleotides used in the production of a silica shell particle is from about 10 to about 25,000 polynucleotides per silica shell particle. In further aspects, the number of polynucleotides used in the production of a silica shell particle is from about 50 to about 10,000 polynucleotides per silica shell particle, and in still further aspects the number of polynucleotides used in the production of a silica shell particle is from about 200 to about 5,000 polynucleotides per silica shell particle. In various aspects, the number of polynucleotides used in the production of a silica shell particle is about 10, about 15, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, about 200, about 205, about 210, about 215, about 220, about 225, about 230, about 235, about 240, about 245, about 250, about 255, about 260, about 265, about 270, about 275, about 280, about 285, about 290, about 295, about 300, about 305, about 310, about 315, about 320, about 325, about 330, about 335, about 340, about 345, about 350, about 355, about 360, about 365, about 370, about 375, about 380, about 385, about 390, about 395, about 400, about 405, about 410, about 415, about 420, about 425, about 430, about 435, about 440, about 445, about 450, about 455, about 460, about 465, about 470, about 475, about 480, about 485, about 490, about 495, about 500, about 505, about 510, about 515, about 520, about 525, about 530, about 535, about 540, about 545, about 550, about 555, about 560, about 565, about 570, about 575, about 580, about 585, about 590, about 595, about 600, about 605, about 610, about 615, about 620, about 625, about 630, about 635, about 640, about 645, about 650, about 655, about 660, about 665, about 670, about 675, about 680, about 685, about 690, about 695, about 700, about 705, about 710, about 715, about 720, about 725, about 730, about 735, about 740, about 745, about 750, about 755, about 760, about 765, about 770, about 775, about 780, about 785, about 790, about 795, about 800, about 805, about 810, about 815, about 820, about 825, about 830, about 835, about 840, about 845, about 850, about 855, about 860, about 865, about 870, about 875, about 880, about 885, about 890, about 895, about 900, about 905, about 910, about 915, about 920, about 925, about 930, about 935, about 940, about 945, about 950, about 955, about 960, about 965, about 970, about 975, about 980, about 985, about 990, about 995, about 1000, about 1100, about 1200, about 1300, about 1400, about 1500, about 1600, about 1700, about 1800, about 1900, about 2000, about 2100, about 2200, about 2300, about 2400, about 2500, about 2600, about 2700, about 2800, about 2900, about 3000, about 3100, about 3200, about 3300, about 3400, about 3500, about 3600, about 3700, about 3800, about 3900, about 4000, about 4100, about 4200, about 4300, about 4400, about 4500, about 4600, about 4700, about 4800, about 4900, about 5000, about 5100, about 5200, about 5300, about 5400, about 5500, about 5600, about 5700, about 5800, about 5900, about 6000, about 6100, about 6200, about 6300, about 6400, about 6500, about 6600, about 6700, about 6800, about 6900, about 7000, about 7100, about 7200, about 7300, about 7400, about 7500, about 7600, about 7700, about 7800, about 7900, about 8000, about 8100, about 8200, about 8300, about 8400, about 8500, about 8600, about 8700, about 8800, about 8900, about 9000, about 9100, about 9200, about 9300, about 9400, about 9500, about 9600, about 9700, about 9800, about 9900, about 10000, about 10100, about 10200, about 10300, about 10400, about 10500, about 10600, about 10700, about 10800, about 10900, about 11000, about 11100, about 11200, about 11300, about 11400, about 11500, about 11600, about 11700, about 11800, about 11900, about 12000, about 12100, about 12200, about 12300, about 12400, about 12500, about 12600, about 12700, about 12800, about 12900, about 13000, about 13100, about 13200, about 13300, about 13400, about 13500, about 13600, about 13700, about 13800, about 13900, about 14000, about 14100, about 14200, about 14300, about 14400, about 14500, about 14600, about 14700, about 14800, about 14900, about 15000, about 15100, about 15200, about 15300, about 15400, about 15500, about 15600, about 15700, about 15800, about 15900, about 16000, about 16100, about 16200, about 16300, about 16400, about 16500, about 16600, about 16700, about 16800, about 16900, about 17000, about 17100, about 17200, about 17300, about 17400, about 17500, about 17600, about 17700, about 17800, about 17900, about 18000, about 18100, about 18200, about 18300, about 18400, about 18500, about 18600, about 18700, about 18800, about 18900, about 19000, about 19100, about 19200, about 19300, about 19400, about 19500, about 19600, about 19700, about 19800, about 19900, about 20000, about 20100, about 20200, about 20300, about 20400, about 20500, about 20600, about 20700, about 20800, about 20900, about 21000, about 21100, about 21200, about 21300, about 21400, about 21500, about 21600, about 21700, about 21800, about 21900, about 22000, about 22100, about 22200, about 22300, about 22400, about 22500, about 22600, about 22700, about 22800, about 22900, about 23000, about 23100, about 23200, about 23300, about 23400, about 23500, about 23600, about 23700, about 23800, about 23900, about 24000, about 24100, about 24200, about 24300, about 24400, about 24500, about 24600, about 24700, about 24800, about 24900, about 25000 or more per silica shell particle.

It is also contemplated that polynucleotide surface density modulates the stability of the polynucleotide associated with the silica shell particle. Thus, in one embodiment, a silica shell particle comprising a polynucleotide is provided wherein the polynucleotide has a half-life that is at least substantially the same as the half-life of an identical polynucleotide that is not part of a silica shell particle. In other embodiments, the polynucleotide associated with the nanoparticle has a half-life that is about 5% greater to about 1,000,000-fold greater or more than the half-life of an identical polynucleotide that is not part of a silica shell particle.

Nanoparticles

As used herein, "nanoparticle" refers to small structures that are less than 10 µm, and preferably less than 5 µm, in any one dimension. The particle can be less than 1 µm in any one dimension. In general, nanoparticles contemplated include any compound or substance with a high loading capacity for an oligonucleotide as described herein. Nanoparticles useful in the practice of the invention include metal (e.g., gold, silver, copper and platinum), semiconductor (e.g., CdSe, CdS, and CdS or CdSe coated with ZnS) and magnetic (e.g., ferromagnetite) colloidal materials, as long as the nanoparticle has the ability to quench the otherwise detectable marker. Other nanoparticles useful in the practice of the invention include ZnS, ZnO, $TiO_2$, AgI, AgBr, $HgI_2$, PbS, PbSe, ZnTe, CdTe, $In_2S_3$, $In_2Se_3$, $Cd_3P_2$, $Cd_3As_2$, InAs, and GaAs.

In some embodiments, the nanoparticle is metallic, and in various aspects, the nanoparticle is a colloidal metal. Thus, in various embodiments, nanoparticles useful in the practice of the methods include metal (including for example and without limitation, gold, silver, platinum, aluminum, palladium, copper, cobalt, iron, indium, nickel, or any other metal amenable to nanoparticle formation), semiconductor (including for example and without limitation, CdSe, CdS, and CdS or CdSe coated with ZnS) and magnetic (for example, ferromagnetite) colloidal materials. Other nanoparticles useful in the practice of the invention include, also without limitation, ZnS, ZnO, Ti, $TiO_2$, Sn, $SnO_2$, Fe, $Fe^{+4}$, $Fe_3O_4$, $Fe_2O_3$, Ag, Cu, Ni, Al, steel, cobalt-chrome alloys, Cd, titanium alloys, AgI, AgBr, $HgI_2$, PbS, PbSe, ZnTe, CdTe, $In_2S_3$, $In_2Se_3$, $Cd_3P_2$, $Cd_3As_2$, InAs, and GaAs. Methods of making ZnS, ZnO, $TiO_2$, AgI, AgBr, $HgI_2$, PbS, PbSe, ZnTe, CdTe, $In_2S_3$, $In_2Se_3$, $Cd_3P_2$, $Cd_3As_2$, InAs, and GaAs nanoparticles are also known in the art. See, e.g., Weller, Angew. Chem. Int. Ed. Engl., 32, 41 (1993); Henglein, Top. Curr. Chem., 143, 113 (1988); Henglein, Chem. Rev., 89, 1861 (1989); Brus, Appl. Phys. A., 53, 465 (1991); Bahncmann, in Photochemical Conversion and Storage of Solar Energy (eds. Pelizetti and Schiavello 1991), page 251; Wang and Herron, J. Phys. Chem., 95, 525 (1991); Olshaysky, et al., J. Am. Chem. Soc., 112, 9438 (1990); Ushida et al., J. Phys. Chem., 95, 5382 (1992).

In practice, compositions and methods are provided using any suitable nanoparticle suitable for use in the disclosed silica shell particles to the extent they do not interfere with silica shell formation, are capable of being removed (e.g., dissolved), and do not interfere with complex formation. The size, shape and chemical composition of the particles contribute to the properties of the resulting silica shell particles. These properties include for example, pore and channel size variation, and choice of dissolving agent. The use of mixtures of particles having different sizes, shapes and/or chemical compositions, as well as the use of nanoparticles having uniform sizes, shapes and chemical composition, is contemplated. Examples of suitable particles include, without limitation, nanoparticles, aggregate particles, and isotropic (such as spherical particles) and anisotropic particles (such as non-spherical rods, tetrahedral, prisms).

Methods of making metal, semiconductor and magnetic nanoparticles are well-known in the art. See, for example, Schmid, G. (ed.) Clusters and Colloids (VCH, Weinheim, 1994); Hayat, M. A. (ed.) Colloidal Gold: Principles, Methods, and Applications (Academic Press, San Diego, 1991); Massart, R., IEEE Transactions On Magnetics, 17, 1247 (1981); Ahmadi, T. S. et al., Science, 272, 1924 (1996); Henglein, A. et al., J. Phys. Chem., 99, 14129 (1995); Curtis, A. C., et al., Angew. Chem. Int. Ed. Engl., 27, 1530 (1988). Preparation of polyalkylcyanoacrylate nanoparticles prepared is described in Fattal, et al., J. Controlled Release (1998) 53: 137-143 and U.S. Pat. No. 4,489,055. Methods for making nanoparticles comprising poly(D-glucaramidoamine)s are described in Liu, et al., J. Am. Chem. Soc. (2004) 126:7422-7423. Preparation of nanoparticles comprising polymerized methylmethacrylate (MMA) is described in Tondelli, et al., Nucl. Acids Res. (1998) 26:5425-5431, and preparation of dendrimer nanoparticles is described in, for example Kukowska-Latallo, et al., Proc. Natl. Acad. Sci. USA (1996) 93:4897-4902 (Starburst polyamidoamine dendrimers).

Also as described in US patent publication No 20030147966, nanoparticles comprising materials described herein are available commercially from, for example, Ted Pella, Inc. (gold), Amersham Corporation (gold) and Nanoprobes, Inc. (gold), or they can be produced from progressive nucleation in solution (e.g., by colloid reaction), or by various physical and chemical vapor deposition processes, such as sputter deposition. See, e.g., HaVashi, (1987) Vac. Sci. Technol. July/August 1987, A5(4):1375-84; Hayashi, (1987) Physics Today, December 1987, pp. 44-60; MRS Bulletin, January 1990, pgs. 16-47.

As further described in US patent publication No 20030147966, nanoparticles contemplated are produced using HAuCl4 and a citrate-reducing agent, using methods known in the art. See, e.g., Marinakos et al., (1999) Adv. Mater. 11: 34-37; Marinakos et al., (1998) Chem. Mater. 10: 1214-19; Enustun & Turkevich, (1963) J. Am. Chem. Soc. 85: 3317. Tin oxide nanoparticles having a dispersed aggregate particle size of about 140 nm are available commercially from Vacuum Metallurgical Co., Ltd. of Chiba, Japan. Other commercially available nanoparticles of various compositions and size ranges are available, for example, from Vector Laboratories, Inc. of Burlingame, Calif.

The size of the nanoparticles can be about 5 nm to about 500 nm (mean diameter), about 10 to about 250 nm, about 10 to about 100 nm, about 30 to about 100 nm, or about 30 to about 300 nm. The size of the nanoparticle is contemplated to be about 5 to about 10 nm, or about 5 to about 20 nm, or about 5 to about 30 nm, or about 5 to about 40 nm, or about 5 to about 60 nm, or about 5 to about 70 nm, or about 5 to about 80 nm, or about 5 to about 90 nm, or about 5 to about 100 nm, or about 5 to about 110 nm, or about 5 to about 120 nm, or about 5 to about 130 nm, or about 5 to about 140 nm, or about 10 to about 20 nm, or about 10 to about 40 nm, or about 10 to about 50 nm, or about 10 to about 60 nm, or about 10 to about 70 nm, or about 10 to about 80 nm, or about 10 to about 90 nm, or about 10 to about 100 nm, or about 10 to about 110 nm, or about 10 to about 120 nm, or about 10 to about 130 nm, or about 10 to about 140 nm, or about 10 to about 150 nm. The nanoparticles may also be rods, prisms, or tetrahedra.

A silica shell is deposited onto the nanoparticle using a silica reagent. A contemplated silica agent is a silicate, such as tetraethyl orthosilicate (TEOS). The thickness of the silica shell can be at least 10 nm, or 250 nm or less. Also contemplated thicknesses include about 20 nm to about 200 nm, about 10 nm to about 100 nm, about 10 nm to about 150 nm, or about 15 to about 250 nm. Other specifically contemplated thicknesses of the silica shell include 10 nm, 15 nm, 20 nm, 25 nm, 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, 150 nm, 155 nm, 160 nm, 165 nm, 170 nm, 175 nm, 180 nm, 185 nm, 190 nm, 195 nm, 200 nm, 205 nm, 210 nm, 215 nm, 220 nm, 225 nm, 230 nm, 235 nm, 240 nm, 245 nm, or 250 nm. The degree of porosity and thickness of the silica shell can be controlled by varying the conditions under which the silica shell is deposited onto the nanoparticle, as discussed below.

The nanoparticles used here can be at least partially removed (e.g., dissolved) once a silica shell is deposited on its surface, to then produce the silica shell particle. In some cases, the nanoparticle is substantially removed to leave a hollow silica shell particle. It will be appreciated that suitable nanoparticle dissolving agents will depend on the chemical makeup of the nanoparticle. Gold nanoparticles, for example, can be dissolved by using iodine ($I_2$) as a nanoparticle dissolving agent. The dissolution of the nanoparticle core can be achieved by using KCN in the presence of oxygen. In further aspects, iodine or aqua regia is used to dissolve a nanoparticle core.

Therapeutic Agents

"Therapeutic agent," "drug" or "active agent" as used herein means any compound useful for therapeutic or diagnostic purposes. The terms as used herein are understood to mean any compound that is administered to a patient for the treatment of a condition that can traverse a cell membrane more efficiently when attached to a silica shell particle of the disclosure than when administered in the absence of a silica shell particle of the disclosure. Specifically contemplated are payload particles, wherein the therapeutic agent is inserted into the hollow core of a silica shell particle as disclosed herein. When administered to a subject, the therapeutic agent can gradually be released from the hollow core, providing a sustained release administration of that therapeutic agent to the subject. In some cases, the biomolecule on the surface is selected as a targeting agent to deliver the therapeutic agent to a desired biological target of the subject (e.g., a biomolecule which recognizes a specific cell, virus, bacteria and a therapeutic agent chosen to modify the activity of that cell, virus, or bacteria).

The present disclosure is applicable to any therapeutic agent for which delivery is desired. Non-limiting examples of such active agents as well as hydrophobic drugs are found in U.S. Pat. No. 7,611,728, which is incorporated by reference herein in its entirety.

Compositions and methods disclosed herein, in various embodiments, are provided wherein the silica shell particle comprises a multiplicity of therapeutic agents. In one aspect, compositions and methods are provided wherein the multiplicity of therapeutic agents are specifically attached to one silica shell particle. In another aspect, the multiplicity of therapeutic agents is specifically attached to more than one silica shell particle.

Therapeutic agents useful in the materials and methods of the present disclosure can be determined by one of ordinary skill in the art. For example and without limitation, and as exemplified herein, one can perform a routine in vitro test to determine whether a therapeutic agent is able to traverse the cell membrane of a cell more effectively when attached to a silica shell particle than in the absence of attachment to the silica shell particle.

In various embodiments, a drug delivery composition is provided comprising a silica shell particle and a therapeutic agent, the therapeutic agent being one that is deliverable at a significantly lower level in the absence of attachment of the therapeutic agent to the silica shell particle compared to the delivery of the therapeutic agent when attached to the silica shell particle, and wherein the ratio of polynucleotide on the silica shell particle to the therapeutic agent attached to the silica shell particle is sufficient to allow transport of the therapeutic agent into a cell. As used herein, "ratio" refers to a number comparison of polynucleotide to therapeutic agent. For example and without limitation, a 1:1 ratio refers to there being one polynucleotide molecule for every therapeutic agent molecule that is attached to a silica shell particle.

In one embodiment, methods and compositions are provided wherein a therapeutic agent is able to traverse a cell membrane more efficiently when attached to a silica shell particle than when it is not attached to the silica shell particle. In various aspects, a therapeutic agent is able to traverse a cell membrane about 2-fold, about 3-fold, about 4-fold, about 5-fold, about 6-fold, about 7-fold, about 8-fold, about 9-fold, about 10-fold, about 20-fold, about 30-fold, about 40-fold, about 50-fold, about 60-fold, about 70-fold, about 80-fold, about 90-fold or about 100-fold or more efficiently when attached to a silica shell particle than when it is not attached to the silica shell particle.

Therapeutic agents include but are not limited to hydrophilic and hydrophobic compounds. Accordingly, therapeutic agents contemplated by the present disclosure include without limitation drug-like molecules, biomolecules and non-biomolecules.

Protein therapeutic agents include, without limitation peptides, enzymes, structural proteins, receptors and other cellular or circulating proteins as well as fragments and derivatives thereof, the aberrant expression of which gives rise to one or more disorders. Therapeutic agents also include, as one specific embodiment, chemotherapeutic agents. Therapeutic agents also include, in various embodiments, a radioactive material.

In various aspects, protein therapeutic agents include cytokines or hematopoietic factors including without limitation IL-1 alpha, IL-1 beta, IL-2, IL-3, IL-4, IL-5, IL-6, IL-11, colony stimulating factor-1 (CSF-1), M-CSF, SCF, GM-CSF, granulocyte colony stimulating factor (G-CSF), interferon-alpha (IFN-alpha), consensus interferon, IFN-beta, IFN-gamma, IL-7, IL-8, IL-9, IL-10, IL-12, IL-13, IL-14, IL-15, IL-16, IL-17, IL-18, erythropoietin (EPO), thrombopoietin (TPO), angiopoietins, for example Ang-1, Ang-2, Ang-4, Ang-Y, the human angiopoietin-like polypeptide, vascular endothelial growth factor (VEGF), angiogenin, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, brain derived neurotrophic factor, ciliary neutrophic factor, ciliary neutrophic factor receptor, cytokine-induced neutrophil chemotactic factor 1, cytokine-induced neutrophil, chemotactic factor 2α, cytokine-induced neutrophil chemotactic factor 2β, β endothelial cell growth factor, endothelin 1, epidermal growth factor, epithelial-derived neutrophil attractant, fibroblast growth factor 4, fibroblast growth factor 5, fibroblast growth factor 6, fibroblast growth factor 7, fibroblast growth factor 8, fibroblast growth factor 8b, fibroblast growth factor 8c, fibroblast growth factor 9, fibroblast growth factor 10, fibroblast growth factor acidic, fibroblast growth factor basic, glial cell line-derived neutrophic factor receptor α1, glial cell line-derived neutrophic factor receptor α2, growth related protein, growth related protein α, growth related protein β, growth related protein γ, heparin binding epidermal growth factor, hepatocyte growth factor, hepatocyte growth factor receptor, insulin-like growth factor I, insulin-like growth factor receptor, insulin-like growth factor II, insulin-like growth factor binding protein, keratinocyte growth factor, leukemia inhibitory factor, leukemia inhibitory factor receptor α, nerve growth factor nerve growth factor receptor, neurotrophin-3, neurotrophin-4, placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor β chain, platelet derived growth factor βB, platelet derived growth factor receptor α, platelet derived growth factor receptor β, pre-B cell growth stimulating factor, stem cell factor receptor, TNF, including TNF0, TNF1, TNF2, transforming growth factor α, transforming growth factor β, transforming growth factor β1, transforming growth factor β1.2, transforming growth factor β2, transforming growth factor β3, transforming growth factor β5, latent transforming growth factor β1, transforming growth factor β binding protein I, transforming growth factor β binding protein II, transforming growth factor β binding protein III, tumor necrosis factor receptor type I, tumor necrosis factor receptor type II, urokinase-type plasminogen activator receptor, vascular endothelial growth factor, and chimeric proteins and biologically or immunologically active fragments thereof. Examples of biologic agents include, but are not limited to, immunomodulating proteins such as cytokines, monoclonal antibodies against tumor antigens, tumor suppressor genes, and cancer vaccines. Examples of interleukins that may be used in conjunction with the compositions and methods of the present invention include, but are not limited to, interleukin 2 (IL-2), and interleukin 4 (IL-4), interleukin 12 (IL-12). Other immuno-modulating agents other than cytokines include, but are not limited to bacillus Calmette-Guerin, levamisole, and octreotide.

As described by the present disclosure, in some aspects therapeutic agents include small molecules. The term "small molecule," as used herein, refers to a chemical compound, for instance a peptidomimetic that may optionally be derivatized, or any other low molecular weight organic compound, either natural or synthetic. Such small molecules may be a therapeutically deliverable substance or may be further derivatized to facilitate delivery.

By "low molecular weight" is meant compounds having a molecular weight of less than 1000 Daltons, typically between 300 and 700 Daltons. Low molecular weight compounds, in various aspects, are about 100, about 150, about 200, about 250, about 300, about 350, about 400, about 450, about 500, about 550, about 600, about 650, about 700, about 750, about 800, about 850, about 900, about 1000 or more Daltons.

The term "drug-like molecule" is well known to those skilled in the art, and includes the meaning of a compound that has characteristics that make it suitable for use in medicine, for example and without limitation as the active agent in a medicament. Thus, for example and without limitation, a drug-like molecule is a molecule that is synthesized by the techniques of organic chemistry, or by techniques of molecular biology or biochemistry, and is in some aspects a small molecule as defined herein. A drug-like molecule, in various aspects, additionally exhibits features of selective interaction with a particular protein or proteins and is bioavailable and/or able to penetrate cellular membranes either alone or in combination with a composition or method of the present disclosure.

In various embodiments, therapeutic agents described in U.S. Pat. No. 7,667,004 (incorporated by reference herein in its entirety) are contemplated for use in the compositions and methods disclosed herein and include, but are not limited to, alkylating agents, antibiotic agents, antimetabolic agents, hormonal agents, plant-derived agents, and biologic agents.

Examples of alkylating agents include, but are not limited to, bischloroethylamines (nitrogen mustards, e.g. chlorambucil, cyclophosphamide, ifosfamide, mechlorethamine, melphalan, uracil mustard), aziridines (e.g. thiotepa), alkyl alkone sulfonates (e.g. busulfan), nitrosoureas (e.g. carmustine, lomustine, streptozocin), nonclassic alkylating agents (altretamine, dacarbazine, and procarbazine), platinum compounds (e.g., carboplastin, cisplatin and platinum (IV) (Pt (IV))).

Examples of antibiotic agents include, but are not limited to, anthracyclines (e.g. doxorubicin, daunorubicin, epirubicin, idarubicin and anthracenedione), mitomycin C, bleomycin, dactinomycin, plicatomycin. Additional antibiotic agents are discussed in detail below.

Examples of antimetabolic agents include, but are not limited to, fluorouracil (5-FU), floxuridine (5-FUdR), methotrexate, leucovorin, hydroxyurea, thioguanine (6-TG), mercaptopurine (6-MP), cytarabine, pentostatin, fludarabine phosphate, cladribine (2-CDA), asparaginase, imatinib mesylate (or GLEEVEC®), and gemcitabine.

Examples of hormonal agents include, but are not limited to, synthetic estrogens (e.g. diethylstibestrol), antiestrogens (e.g. tamoxifen, toremifene, fluoxymesterol and raloxifene), antiandrogens (bicalutamide, nilutamide, flutamide), aromatase inhibitors (e.g., aminoglutethimide, anastrozole and tetrazole), ketoconazole, goserelin acetate, leuprolide, megestrol acetate and mifepristone.

Examples of plant-derived agents include, but are not limited to, vinca alkaloids (e.g., vincristine, vinblastine, vindesine, vinzolidine and vinorelbine), podophyllotoxins (e.g., etoposide (VP-16) and teniposide (VM-26)), camptothecin compounds (e.g., 20(S) camptothecin, topotecan, rubitecan, and irinotecan), taxanes (e.g., paclitaxel and docetaxel).

Chemotherapeutic agents contemplated for use include, without limitation, alkylating agents including: nitrogen mustards, such as mechlor-ethamine, cyclophosphamide, ifosfamide, melphalan and chlorambucil; nitrosoureas, such as carmustine (BCNU), lomustine (CCNU), and semustine (methyl-CCNU); ethylenimines/methylmelamine such as thriethylenemelamine (TEM), triethylene, thiophosphoramide (thiotepa), hexamethylmelamine (HMM, altretamine); alkyl sulfonates such as busulfan; triazines such as dacarbazine (DTIC); antimetabolites including folic acid analogs such as methotrexate and trimetrexate, pyrimidine analogs such as 5-fluorouracil, fluorodeoxyuridine, gemcitabine, cytosine arabinoside (AraC, cytarabine), 5-azacytidine, 2,2'-difluorodeoxycytidine, purine analogs such as 6-mercaptopurine, 6-thioguanine, azathioprine, 2'-deoxycoformycin (pentostatin), erythrohydroxynonyladenine (EHNA), fludarabine phosphate, and 2-chlorodeoxyadenosine (cladribine, 2-CdA); natural products including antimitotic drugs such as paclitaxel, vinca alkaloids including vinblastine (VLB), vincristine, and vinorelbine, taxotere, estramustine, and estramustine phosphate; epipodophylotoxins such as etoposide and teniposide; antibiotics such as actimomycin D, daunomycin (rubidomycin), doxorubicin, mitoxantrone, idarubicin, bleomycins, plicamycin (mithramycin), mitomycinC, and actinomycin; enzymes such as L-asparaginase; biological response modifiers such as interferon-alpha, IL-2, G-CSF and GM-CSF; miscellaneous agents including platinum coordination complexes such as cisplatin, Pt(IV) and carboplatin, anthracenediones such as mitoxantrone, substituted urea such as hydroxyurea, methylhydrazine derivatives including N-methylhydrazine (MIH) and procarbazine, adrenocortical suppressants such as mitotane (o,p'-DDD) and aminoglutethimide; hormones and antagonists including adrenocorticosteroid antagonists such as prednisone and equivalents, dexamethasone and aminoglutethimide; progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; and non-steroidal antiandrogens such as flutamide.

Antibiotic Compositions

In some aspects, the additional agent can be an antibiotic composition, or in other aspects the silica shell particle itself functions as an antibiotic composition. Accordingly, in some embodiments the present disclosure provides antibiotic compositions comprising a silica shell particle as described herein. Antibiotic compositions as part of functionalized nanoparticles are also described in PCT/US2010/020558, which is incorporated herein by reference in its entirety.

In aspects wherein the silica shell particle comprises a polynucleotide as either a structural biomolecule or a non-structural additional agent, it is contemplated in certain aspects that the polynucleotide is sufficiently complementary to a target coding or non-coding sequence of a prokaryotic gene that it will hybridize to the target sequence under conditions that allow hybridization. In various embodiments, it is contemplated that hybridization of the silica shell particle comprising a polynucleotide to a prokaryotic gene inhibits (or prevents) the growth of a prokaryotic cell. Thus, the hybridization of the silica shell particle comprising a polynucleotide to a prokaryotic gene is contemplated to result in a bacteriostatic or bactericidal effect in aspects wherein the prokaryote is bacteria. In aspects wherein the hybridization occurs in vivo, the growth of the prokaryotic cell is inhibited compared to the growth of the prokaryotic cell in the absence of contact with the polynucleotide-modified nanoparticle.

In some embodiments, hybridization of the silica shell particle comprising a polynucleotide to a prokaryotic gene inhibits expression of a functional prokaryotic protein encoded by the prokaryotic gene. A "functional prokaryotic protein" as used herein refers to a full length wild type protein encoded by a prokaryotic gene, and in certain aspects, the functional protein is essential for prokaryotic cell growth.

Prokaryotic proteins essential for growth include, but are not limited to, a gram-negative gene product, a gram-positive gene product, cell cycle gene product, a gene product involved in DNA replication, a cell division gene product, a gene product involved in protein synthesis, a bacterial gyrase, and an acyl carrier gene product. These classes are discussed in detail herein below.

The present disclosure also contemplates an antibiotic composition wherein hybridization to a target non-coding sequence of a prokaryotic gene results in expression of a protein encoded by the prokaryotic gene with altered activity. In some embodiments, the antibiotic composition hybridizes to a target non-coding sequence of a prokaryotic gene that confers a resistance to an antibiotic. These genes are known to those of ordinary skill in the art and are discussed, e.g., in Liu et al., *Nucleic Acids Research* 37: D443-D447, 2009 (incorporated herein by reference in its entirety). In some aspects, hybridization of the antibiotic composition to a target non-coding sequence of a prokaryotic gene that confers a resistance to an antibiotic results in increasing the susceptibility of the prokaryote to an antibiotic. In one aspect, the susceptibility of the prokaryote to the antibiotic is increased compared to the susceptibility of the prokaryote that was not contacted with the antibiotic composition. Relative susceptibility to an antibiotic can be determined by those of ordinary skill in the art using routine techniques as described herein.

Biomolecule Markers/Labels

A biomolecule as described herein, in various aspects, optionally comprises a detectable label. Accordingly, the disclosure provides compositions and methods wherein biomolecule complex formation is detected by a detectable change. In one aspect, complex formation gives rise to a color change which is observed with the naked eye or spectroscopically.

Methods for visualizing the detectable change resulting from biomolecule complex formation also include any fluorescent detection method, including without limitation fluorescence microscopy, a microtiter plate reader or fluorescence-activated cell sorting (FACS).

It will be understood that a label contemplated by the disclosure includes any of the fluorophores described herein as well as other detectable labels known in the art. For example, labels also include, but are not limited to, redox active probes, chemiluminescent molecules, radioactive labels, dyes, fluorescent molecules, phosphorescent molecules, imaging and/or contrast agents as described below, quantum dots, as well as any marker which can be detected using spectroscopic means, i.e., those markers detectable using microscopy and cytometry. In aspects of the disclosure wherein a detectable label is to be detected, the disclosure provides that any luminescent, fluorescent, or phosphorescent molecule or particle can be efficiently quenched by noble metal surfaces. Accordingly, each type of molecule is contemplated for use in the compositions and methods disclosed.

Methods of labeling biomolecules with fluorescent molecules and measuring fluorescence are well known in the art.

Suitable fluorescent molecules are also well known in the art and include without limitation 1,8-ANS (1-Anilinonaphthalene-8-sulfonic acid), 1-Anilinonaphthalene-8-sulfonic acid (1,8-ANS),5-(and-6)-Carboxy-2',7'-dichlorofluorescein pH 9.0, 5-FAM pH 9.0, 5-ROX (5-Carboxy-X-rhodamine, triethylammonium salt), 5-ROX pH 7.0, 5-TAMRA, 5-TAMRA pH 7.0, 5-TAMRA-MeOH, 6 JOE, 6,8-Difluoro-7-hydroxy-4-methylcoumarin pH 9.0, 6-Carboxyrhodamine 6G pH 7.0, 6-Carboxyrhodamine 6G, hydrochloride, 6-HEX, SE pH 9.0, 6-TET, SE pH 9.0, 7-Amino-4-methylcoumarin pH 7.0, 7-Hydroxy-4-methylcoumarin, 7-Hydroxy-4-methylcoumarin pH 9.0, Alexa 350, Alexa 405, Alexa 430, Alexa 488, Alexa 532, Alexa 546, Alexa 555, Alexa 568, Alexa 594, Alexa 647, Alexa 660, Alexa 680, Alexa 700, Alexa Fluor 430 antibody conjugate pH 7.2, Alexa Fluor 488 antibody conjugate pH 8.0, Alexa Fluor 488 hydrazide-water, Alexa Fluor 532 antibody conjugate pH 7.2, Alexa Fluor 555 antibody conjugate pH 7.2, Alexa Fluor 568 antibody conjugate pH 7.2, Alexa Fluor 610 R-phycoerythrin streptavidin pH 7.2, Alexa Fluor 647 antibody conjugate pH 7.2, Alexa Fluor 647 R-phycoerythrin streptavidin pH 7.2, Alexa Fluor 660 antibody conjugate pH 7.2, Alexa Fluor 680 antibody conjugate pH 7.2, Alexa Fluor 700 antibody conjugate pH 7.2, Allophycocyanin pH 7.5, AMCA conjugate, Amino Coumarin, APC (allophycocyanin), Atto 647, BCECF pH 5.5, BCECF pH 9.0, BFP (Blue Fluorescent Protein), BO-PRO-1-DNA, BO-PRO-3-DNA, BOBO-1-DNA, BOBO-3-DNA, BODIPY 650/665-X, MeOH, BODIPY FL conjugate, BODIPY FL, MeOH, Bodipy R6G SE, BODIPY R6G, MeOH, BODIPY TMR-X antibody conjugate pH 7.2, Bodipy TMR-X conjugate, BODIPY TMR-X, MeOH, BODIPY TMR-X, SE, BODIPY TR-X phallacidin pH 7.0, BODIPY TR-X, MeOH, BODIPY TR-X, SE, BOPRO-1, BOPRO-3, Calcein, Calcein pH 9.0, Calcium Crimson, Calcium Crimson Ca2+, Calcium Green, Calcium Green-1 Ca2+, Calcium Orange, Calcium Orange Ca2+, Carboxynaphthofluorescein pH 10.0, Cascade Blue, Cascade Blue BSA pH 7.0, Cascade Yellow, Cascade Yellow antibody conjugate pH 8.0, CFDA, CFP (Cyan Fluorescent Protein), CI-NERF pH 2.5, CI-NERF pH 6.0, Citrine, Coumarin, Cy 2, Cy 3, Cy 3.5, Cy 5, Cy 5.5, CyQUANT GR-DNA, Dansyl Cadaverine, Dansyl Cadaverine, MeOH, DAPI, DAPI-DNA, Dapoxyl(2-aminoethyl)sulfonamide, DDAO pH 9.0, Di-8 ANEPPS, Di-8-ANEPPS-lipid, DiI, DiO, DM-NERF pH 4.0, DM-NERF pH 7.0, DsRed, DTAF, dTomato, eCFP (Enhanced Cyan Fluorescent Protein), eGFP (Enhanced Green Fluorescent Protein), Eosin, Eosin antibody conjugate pH 8.0, Erythrosin-5-isothiocyanate pH 9.0, Ethidium Bromide, Ethidium homodimer, Ethidium homodimer-1-DNA, eYFP (Enhanced Yellow Fluorescent Protein), FDA, FITC, FITC antibody conjugate pH 8.0, FlAsH, Fluo-3, Fluo-3 Ca2+, Fluo-4, Fluor-Ruby, Fluorescein, Fluorescein 0.1 M NaOH, Fluorescein antibody conjugate pH 8.0, Fluorescein dextran pH 8.0, Fluorescein pH 9.0, Fluoro-Emerald, FM 1-43, FM 1-43 lipid, FM 4-64, FM 4-64, 2% CHAPS, Fura Red Ca2+, Fura Red, high Ca, Fura Red, low Ca, Fura-2 Ca2+, Fura-2, high Ca, Fura-2, no Ca, GFP (S65T), HcRed, Hoechst 33258, Hoechst 33258-DNA, Hoechst 33342, Indo-1 Ca2+, Indo-1, Ca free, Indo-1, Ca saturated, JC-1, JC-1 pH 8.2, Lissamine rhodamine, LOLO-1-DNA, Lucifer Yellow, CH, LysoSensor Blue, LysoSensor Blue pH 5.0, LysoSensor Green, LysoSensor Green pH 5.0, LysoSensor Yellow pH 3.0, LysoSensor Yellow pH 9.0, LysoTracker Blue, LysoTracker Green, LysoTracker Red, Magnesium Green, Magnesium Green Mg2+, Magnesium Orange, Marina Blue, mBanana, mCherry, mHoneydew, MitoTracker Green, MitoTracker Green FM, MeOH, MitoTracker Orange, MitoTracker Orange, MeOH, MitoTracker Red, MitoTracker Red, MeOH, mOrange, mPlum, mRFP, mStrawberry, mTangerine, NBD-X, NBD-X, MeOH, NeuroTrace 500/525, green fluorescent Niss1 stain-RNA, Nile Blue, EtOH, Nile Red, Nile Red-lipid, Niss1, Oregon Green 488, Oregon Green 488 antibody conjugate pH 8.0, Oregon Green 514, Oregon Green 514 antibody conjugate pH 8.0, Pacific Blue, Pacific Blue antibody conjugate pH 8.0, Phycoerythrin, PicoGreen dsDNA quantitation reagent, PO-PRO-1, PO-PRO-1-DNA, PO-PRO-3, PO-PRO-3-DNA, POPO-1, POPO-1-DNA, POPO-3, Propidium Iodide, Propidium Iodide-DNA, R-Phycoerythrin pH 7.5, ReAsH, Resorufin, Resorufin pH 9.0, Rhod-2, Rhod-2 Ca2+, Rhodamine, Rhodamine 110, Rhodamine 110 pH 7.0, Rhodamine 123, MeOH, Rhodamine Green, Rhodamine phalloidin pH 7.0, Rhodamine Red-X antibody conjugate pH 8.0, Rhodaminen Green pH 7.0, Rhodol Green antibody conjugate pH 8.0, Sapphire, SBFI-Na+, Sodium Green Na+, Sulforhodamine 101, EtOH, SYBR Green I, SYPRO Ruby, SYTO 13-DNA, SYTO 45-DNA, SYTOX Blue-DNA, Tetramethylrhodamine antibody conjugate pH 8.0, Tetramethylrhodamine dextran pH 7.0, Texas Red-X antibody conjugate pH 7.2, TO-PRO-1-DNA, TO-PRO-3-DNA, TOTO-1-DNA, TOTO-3-DNA, TRITC, X-Rhod-1 Ca2+, YO-PRO-1-DNA, YO-PRO-3-DNA, YOYO-1-DNA, and YOYO-3-DNA.

It is also contemplated by the disclosure that, in some aspects, fluorescent polypeptides are used. Any detectable polypeptide known in the art is useful in the methods of the disclosure, and in some aspects is a fluorescent protein.

Contrast Agents

Disclosed herein are, in various aspects, methods and compositions comprising a silica shell particle, wherein the biomolecule is a polynucleotide, and wherein the polynucleotide is conjugated to a contrast agent through a conjugation site. In further aspects, a contrast agent is conjugated to any other biomolecule as described herein. As used herein, a "contrast agent" is a compound or other substance introduced into a cell in order to create a difference in the apparent density of various organs and tissues, making it easier to see the delineate adjacent body tissues and organs. It will be understood that conjugation of a contrast agent to any biomolecule described herein is useful in the compositions and methods of the disclosure.

Methods provided by the disclosure include those wherein relaxivity of the contrast agent in association with a silica shell particle is increased relative to the relaxivity of the contrast agent in the absence of being associated with a nanoparticle. In some aspects, the increase is about 1-fold to about 20-fold. In further aspects, the increase is about 2-fold fold to about 10-fold, and in yet further aspects the increase is about 3-fold.

In some embodiments, the contrast agent is selected from the group consisting of gadolinium, xenon, iron oxide, a manganese chelate (Mn-DPDP) and copper. Thus, in some embodiments the contrast agent is a paramagnetic compound, and in some aspects, the paramagnetic compound is gadolinium.

The present disclosure also contemplates contrast agents that are useful for positron emission tomography (PET) scanning. In some aspects, the PET contrast agent is a radionuclide. In certain embodiments the contrast agent comprises a PET contrast agent comprising a label selected from the group consisting of $^{11}C$, $^{13}N$, $^{18}F$, $^{64}Cu$, $^{68}Ge$, $^{99m}Tc$ and $^{82}Ru$. In particular embodiments the contrast agent is a PET contrast agent selected from the group consisting of [$^{11}C$] choline, [$^{18}F$]fluorodeoxyglucose (FDG), [$^{11}C$]methionine, [$^{11}C$]choline, [$^{11}C$]acetate, [$^{18}F$]fluorocholine, $^{64}Cu$ chelates, $^{99m}Tc$ chelates, and [$^{18}F$]polyethyleneglycol stilbenes.

The disclosure also provides methods wherein a PET contrast agent is introduced into a polynucleotide during the polynucleotide synthesis process or is conjugated to a nucleotide following polynucleotide synthesis. For example and without limitation, nucleotides can be synthesized in which one of the phosphorus atoms is replaced with $^{32}P$ or $^{33}P$, one of the oxygen atoms in the phosphate group is replaced with $^{35}S$, or one or more of the hydrogen atoms is replaced with $^{3}H$. A functional group containing a radionuclide can also be conjugated to a nucleotide through conjugation sites.

The MRI contrast agents can include, but are not limited to positive contrast agents and/or negative contrast agents. Positive contrast agents cause a reduction in the $T_1$ relaxation time (increased signal intensity on $T_1$ weighted images). They (appearing bright on MRI) are typically small molecular weight compounds containing as their active element gadolinium, manganese, or iron. All of these elements have unpaired electron spins in their outer shells and long relaxivities. A special group of negative contrast agents (appearing dark on MRI) include perfluorocarbons (perfluorochemicals), because their presence excludes the hydrogen atoms responsible for the signal in MR imaging.

The composition of the disclosure, in various aspects, is contemplated to comprise a silica shell particle that comprises about 50 to about $2.5 \times 10^6$ contrast agents. In some embodiments, the silica shell particle comprises about 500 to about $1 \times 10^6$ contrast agents.

Targeting Moieties

The term "targeting moiety" as used herein refers to any molecular structure which assists a compound or other molecule in binding or otherwise localizing to a particular target, a target area, entering target cell(s), or binding to a target receptor. For example and without limitation, targeting moieties may include proteins, including antibodies and protein fragments capable of binding to a desired target site in vivo or in vitro, peptides, small molecules, anticancer agents, polynucleotide-binding agents, carbohydrates, ligands for cell surface receptors, aptamers, lipids (including cationic, neutral, and steroidal lipids, virosomes, and liposomes), antibodies, lectins, ligands, sugars, steroids, hormones, and nutrients, may serve as targeting moieties. Targeting moieties are useful for delivery of the silica shell particle to specific cell types and/or organs, as well as sub-cellular locations.

In some embodiments, the targeting moiety is a protein. The protein portion of the composition of the present disclosure is, in some aspects, a protein capable of targeting the composition to target cell. The targeting protein of the present disclosure may bind to a receptor, substrate, antigenic determinant, or other binding site on a target cell or other target site.

Antibodies useful as targeting proteins may be polyclonal or monoclonal. A number of monoclonal antibodies (MAbs) that bind to a specific type of cell have been developed. Antibodies derived through genetic engineering or protein engineering may be used as well.

The antibody employed as a targeting agent in the present disclosure may be an intact molecule, a fragment thereof, or a functional equivalent thereof. Examples of antibody fragments useful in the compositions of the present disclosure are F(ab')$_2$, Fab' Fab and Fv fragments, which may be produced by conventional methods or by genetic or protein engineering.

In some embodiments, the polynucleotide portion of the silica shell particle may serve as an additional or auxiliary targeting moiety. The polynucleotide portion may be selected or designed to assist in extracellular targeting, or to act as an intracellular targeting moiety. That is, the polynucleotide portion may act as a DNA probe seeking out target cells. This additional targeting capability will serve to improve specificity in delivery of the composition to target cells. The polynucleotide may additionally or alternatively be selected or designed to target the composition within target cells, while the targeting protein targets the conjugate extracellularly.

It is contemplated that the targeting moiety can, in various embodiments, be associated with a silica shell particle. In aspects wherein the silica shell particle comprises a nanoparticle, it is contemplated that the targeting moiety is attached to either the nanoparticle, the biomolecule or both. In further aspects, the targeting moiety is associated with the silica shell particle composition, and in other aspects the targeting moiety is administered before, concurrent with, or after the administration of a composition of the disclosure.

Methods of Preparing Silica Shell Particles

In a representative example, to prepare the silica ($SiO_2$) shells, 13 nm citrate-stabilized gold nanoparticles (Au NP) were synthesized to serve as sacrificial templates. (20,21) The Au NPs were passivated with a short poly(ethylene glycol) (PEG) chain containing a thiol functional group on one end and a carboxylic acid on the other (SH—$(CH_2)_{11}$-$(EG)_6$-

OCH$_2$—COOH) and redispersed in ethanol. The Au NPs were directly coated with a thin layer (~15 nm) of silica using an ammonia-catalyzed hydrolysis of tetraethyl orthosilicate (TEOS) and subsequent condensation of silicic acid to give a network of tetrahedral SiO$_4$ units with shared vertices. (22) The thickness of the silica shell can easily be controlled by changing the relative concentrations of Au NPs, water, ammonia, and silicon alkoxide in the reaction. (23) The resulting Au core-silica shell (Au@SiO$_2$) particles were heated at 60° C. for 24 h to ensure a homogeneous silica shell. (24)

To achieve a dense layer of DNA on the silica shell surface, the heterobifunctional cross-linker p-maleimidophenyl isocyanate (PMPI) was used since cross-linkers with amine-reactive isocyanates have demonstrated improved retention of maleimide activity compared with NHS-ester based linkers. (25) The Au@SiO$_2$ NPs were first derivatized with (aminopropyl)-triethoxysilane (APTES) and subsequently activated with amine-reactive PMPI to introduce thiol-reactive maleimide groups. (25) The addition of DNA oligonucleotides designed to target an mRNA sequence coding for enhanced green fluorescent protein (eGFP) with terminal propylthiol groups (3'-SH(C$_3$H$_6$)-AAAAAAAAAGGTGT-TCAAGTCGCACAGGC-5') (SEQ ID NO: 1), followed by the slow addition of NaCl to 0.3 M, led to the formation of polyvalent Au@SiO$_2$ particles with a loading of ~75 strands per particle. Upon selective oxidative dissolution of the Au NP core with I$_2$, hollow SiO$_2$ SNAs are formed (FIG. 1). Finally, the silica SNAs were dialyzed overnight against water to remove I$_2$ remaining in solution.

Figure 2:
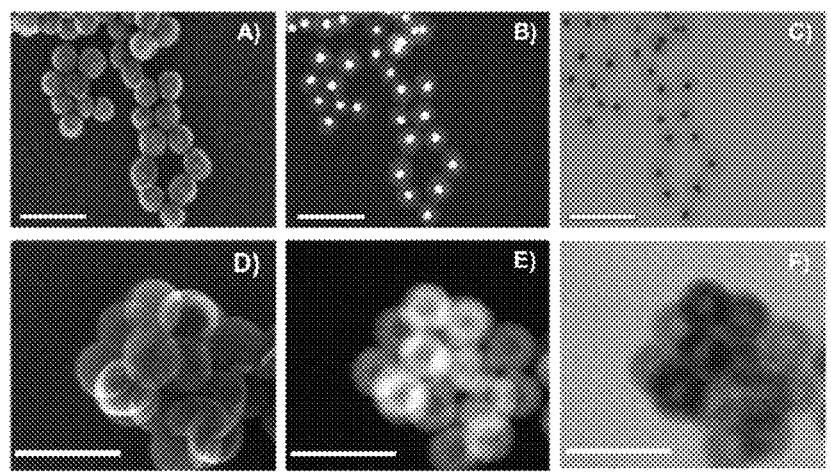
FIG. 2. STEM images of Au@$SiO_2$ particles (A-C) and hollow $SiO_2$ particles (D-F) in scanning, z-contrast, and transmission modes, respectively. In A-C, the Au NP cores are visible. After the addition of $I_2$, the Au NP cores dissolve leaving a hollow interior (E-F). Scale bars are 100 nm.

The ability of I$_2$ to oxidatively dissolve the gold core indicates that the silica shells remain porous through the heating and DNA functionalization steps. The Au@SiO$_2$ and gold-free SiO$_2$ particles were characterized by scanning transmission electron microscopy (STEM) in scanning, z-contrast, and transmission modes (FIGS. 2A-C and D-F, respectively). Indeed, the microscopy images indicate that the Au NP cores are entirely dissolved upon the addition of I$_2$ and a hollow interior remains. Importantly, the silica shells remain as discrete particles and maintain their structure upon dissolution of the gold core, a conclusion also verified by dynamic light scattering (DLS).

Figure 3:
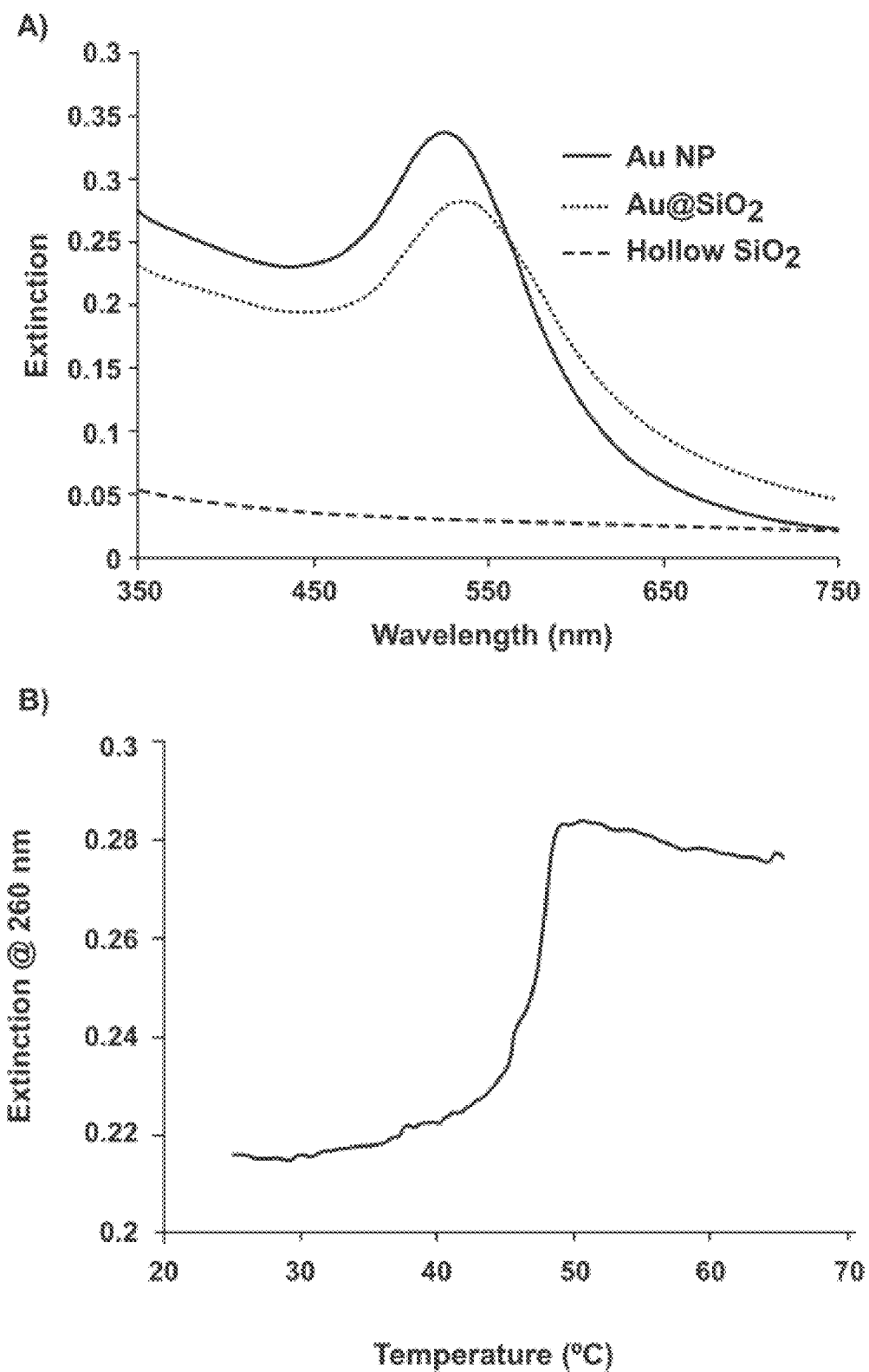
FIG. 3. (A) Extinction spectra of Au NP templates, silica-coated Au NPs (Au@$SiO_2$), and hollow $SiO_2$ particles resulting from the treatment of the Au@$SiO_2$ particles with $I_2$. The Au@$SiO_2$ particles exhibit a distinct absorption at ~530 nm that is characteristic of Au NP, albeit slightly red-shifted due to the silica shell. After treatment with $I_2$, the hollow $SiO_2$ particles do not contain this absorption band, confirming the dissolution of the Au NP core. (B) Melting analysis of DNA functionalized $SiO_2$ particles hybridized using a self-complementary linker. The sharp melting transition (full-width half-max (FWHM)=~2° C.) is indicative of cooperative binding.

Initially the Au NPs had an average hydrodynamic radius of 17.3±0.8 nm. After the deposition of the silica shells onto the Au NP templates, this value increased to 47.7±10.1 nm. Upon functionalization with DNA using APTES and PMPI, the final hydrodynamic radius was measured to be 85.8±16.4 nm. It should be noted that the DLS measurements of the hydrated particles are slightly larger than the diameters of the dry particles measured with electron microscopy. (26) However, the trend in the DLS data is indicative of growth at each step in the synthesis without the formation of large aggregates. The synthesis of the silica SNAs was also monitored with UV-vis spectroscopy (FIG. 3A). The UV-vis spectra reveal that the Au@SiO$_2$ particles exhibit a distinct absorption at ~530 nm that is characteristic of dispersed gold nanoparticles albeit slightly red-shifted compared to Au NPs due to the increase in the dielectric constant of the silica shell. (27-29) After the addition of I$_2$, the absorption band at 530 nm is no longer present, consistent with the removal of the Au core.

Previously, we have shown that SNAs, when hybridized with complementary oligonucleotides, exhibit narrow melting transitions compared with free DNA strands due to a high degree of cooperative binding. (30) This phenomenon is also observed for hollow SNAs consisting of cross-linked nucleic acids. (13) Due to the layer of highly oriented oligonucleotides on the surface of the silica shells (~75 DNA strands per particle when salted to 0.3 M NaCl, determined by the Oli-Green Assay), it was hypothesized that both the Au@SiO$_2$ particles and the hollow silica SNAs would exhibit cooperative binding behavior as well. Upon the addition of a self-complementary linker strand that binds to the oligonucleotides on the silica surface, the particles formed visible aggregates, which were then dehybridized by slowly increasing the temperature. As shown in FIG. 3B, the aggregated SiO$_2$ particles exhibit a sharp melting transition (FWHW of the derivative=~2° C.), indicative of cooperative behavior. (2)

Figure 4:
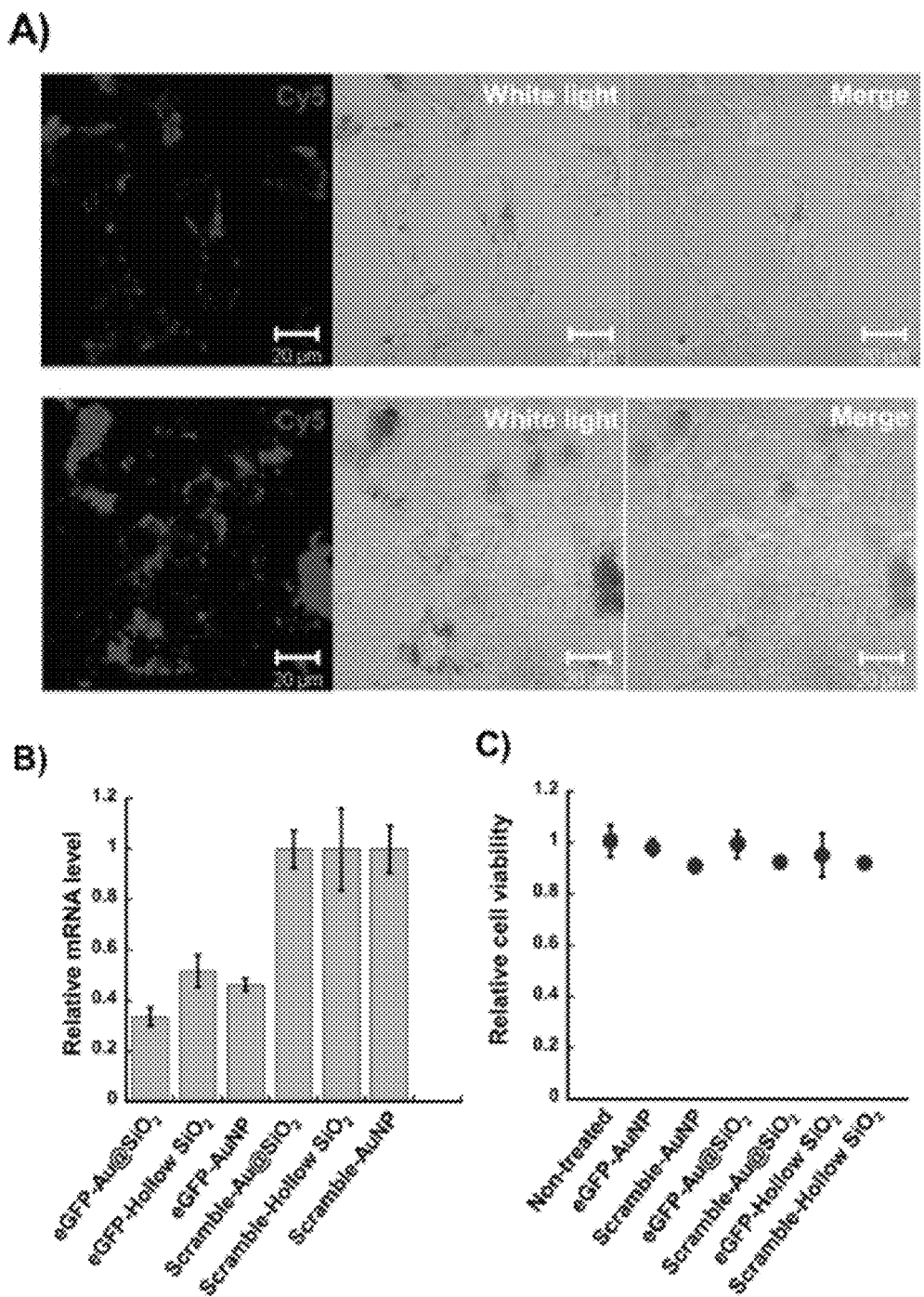
FIG. 4. Cellular uptake and response of the DNA functionalized Au@$SiO_2$ and hollow $SiO_2$ particles in C166 cells. (A) C166 cells were treated with Au@$SiO_2$ particles (upper panel) and hollow $SiO_2$ particles (lower panel) functionalized with Cy5 dye-labeled anti-eGFP DNA oligonucleotides. Cy5 fluorescence is observed in the cytoplasm, but not in the nuclei, indicating the internalization of the particles into the cells. Scale bars are 20 μm. (B) eGFP knockdown at the mRNA level determined by qRT-PCR. mRNA levels of cells treated with anti-eGFP DNA oligonucleotide functionalized Au@$SiO_2$ and hollow $SiO_2$ particles were significantly reduced when compared with those treated with scrambled-sequence DNA particles. (C) Minimal cell toxicity of the Au@$SiO_2$ and hollow $SiO_2$ particles toward C166 cells was detected using the MTT assay. Cells treated with the eGFP-targeted and nontargeted DNA oligonucleotides showed up to 95% viability compared with nontreated cells.

Once it was confirmed that the Au@SiO$_2$ and core-free SiO$_2$ SNAs retain the cooperative binding properties of Au NPs densely functionalized with nucleic acids, the ability of these particles to be transfected into cells and facilitate gene regulation via the antisense pathway was investigated. To qualitatively access the cellular uptake of the SiO$_2$ SNAs, particles with and without the Au NP core were functionalized with Cy5 dye-labeled anti-eGFP DNA oligonucleotides. The particles (5 nM) were then incubated overnight with C166 mouse endothelial cells stably expressing the eGFP gene. It is important to note that no cationic transfection agent was included during the incubation step. The C166 cells were washed, fixed, and imaged by laser scanning confocal microscopy. As shown in FIG. 4A, both the Au@SiO$_2$ and the hollow SiO$_2$ particles are taken into the cytoplasm of the C166 cells. The mechanism of cellular uptake of SNAs has previously been demonstrated to involve receptor-mediated endocytosis (8) and stems from the dense, highly oriented layer of nucleic acids. (2) It is therefore hypothesized that a similar mechanism applies for the DNA functionalized Au@SiO$_2$ and hollow SiO$_2$ particles. Note that neither of these particles enter the nuclei of the cells because of their size. Images of planes collected at various depths within the cell samples (z-stack) further confirmed cellular uptake.

The silica-based SNAs were next evaluated for their ability to regulate target genes. Au@SiO$_2$ particles, hollow SiO$_2$ particles, and Au NPs were functionalized with anti-eGFP DNA oligonucleotides and incubated (5 nM) with C166 cells stably expressing eGFP. Particles functionalized with nontargeting scrambled DNA oligonucleotides served as a negative control. The cells were then collected, lysed, and analyzed for their eGFP mRNA levels by quantitative real-time reverse transcriptase polymerase chain reaction (qRT-PCR). mRNA levels of cells treated with anti-eGFP Au@SiO$_2$ particles and core-free SiO$_2$ shells were significantly reduced by 68% and 50%, respectively, when compared with those treated with scrambled "nonsense" DNA particles (FIG. 4B). Importantly, the amount of knockdown is comparable to that observed with DNA functionalized Au NPs (~52%). Furthermore, the Au@SiO$_2$ particles and hollow SiO$_2$ SNAs were shown to exhibit low cytotoxicity toward C166 cells using the 3-(4,5-dimethylthiazol-2-yl)-2,5-diphenyl tetrazolium bromide (MTT) assay. As indicated in FIG. 4C, cells treated with the targeted and nontargeted DNA oligonucleotides for 8 h showed up to 95% viability compared with a nontreated control. Taken together, these data suggest that this new class of core-free SNA retains the unique properties of the Au NP SNAs, including efficient cellular uptake without the need for conventional cationic transfection agents, a high capacity for gene regulation, and low cytotoxicity.

The present work describes a simple, scalable, and biocompatible SNA construct that serves to confirm our hypothesis that the emergent properties of SNAs are a result of the layer of oriented oligonucleotides and not the inorganic nanoparticle core. The use of silica as the cross-linking reagent makes this construct extremely versatile; the thickness and porosity of the silica shell is tunable with reaction conditions, and many well-established coupling chemistries including EDC/NHS-ester, (31) copper-catalyzed (32) or copper-free (33) click chemistry, and reductive amination (34) can be utilized to achieve a densely packed, oriented nucleic acid shell. Additionally, there are potential benefits of a hollow architecture including tunable degradation profiles and the ability to load the hollow interior with biologically relevant molecules or drugs. Indeed, these novel core-free $SiO_2$ SNAs represent a new class of SNA that shows promise for a wide range of intracellular gene regulation applications and, therefore, constitutes a new class of nanotherapeutics.

Methods of Using Silica Shell Particles

Silica shell particles are useful, in some embodiments, as a delivery vehicle. Thus, a silica shell particle is made wherein, in one aspect, an additional agent as defined herein is localized inside the particle. In related aspects, the additional agent is associated with the silica shell particle as described herein. It is contemplated that the silica shell particle that is utilized as a delivery vehicle is, in some aspects, made more porous, so as to allow placement of the additional agent inside the silica shell particle. Porosity of the silica shell particle can be empirically determined depending on the particular application, and is within the skill in the art. All of the advantages of the functionalized nanoparticle (for example and without limitation, increased cellular uptake and resistance to nuclease degradation) are imparted on the hollow silica shell particle.

It is further contemplated that in some aspects the silica shell particle used as a delivery vehicle is produced with a biomolecule that is at least partially degradable, such that once the silica shell particle is targeted to a location of interest, it dissolves or otherwise degrades in such a way as to release the additional agent. Biomolecule degradation pathways are known to those of skill in the art and can include, without limitation, nuclease pathways, protease pathways and ubiquitin pathways.

In some aspects, a composition of the disclosure acts as a sustained-release formulation. In these aspects, the silica shell particle is produced using poly-lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition [Lewis, "Controlled release of bio active agents from lactide/glycolide polymer," in: M. Chasin and R. Langer (Eds.), Biodegradable Polymers as Drug Delivery Systems (Marcel Dekker: New York, 1990), pp. 1-41, incorporated by reference herein in its entirety].

Methods of Increasing Hybridization Rate

In some embodiments, the biomolecule attached to a silica shell particle is a polynucleotide. Accordingly, methods provided include those that enable an increased rate of association of a polynucleotide with a target polynucleotide through the use of a sicPN. The increase in rate of association is, in various aspects, from about 2-fold to about 100-fold relative to a rate of association in the absence of a sicPN. According to the disclosure, the polynucleotide that associates with the target polynucleotide is part of a silica shell particle. Additionally, a sicPN is added that overlaps with a portion of the target polynucleotide binding site on the polynucleotide used to produce the silica shell particle, but not the complete sequence.

A sicPN (short internal complementary polynucleotide) is a polynucleotide that associates with a polynucleotide that is part of a silica shell particle, and that is displaced and/or released when a target polynucleotide hybridizes to the polynucleotide that is part of the silica shell particle. In one aspect, the sicPN has a lower binding affinity or binding avidity for the polynucleotide that is part of the silica shell particle such that association of the target molecule with the polynucleotide that is part of the silica shell particle causes the sicPN to be displaced and/or released from its association with the polynucleotide that is part of the silica shell particle.

"Displace" as used herein means that a sicPN is partially denatured from its association with a polynucleotide. A displaced sicPN is still in partial association with the polynucleotide to which it is associated. "Release" as used herein means that the sicPN is sufficiently displaced (i.e., completely denatured) so as to cause its disassociation from the polynucleotide to which it is associated. In some aspects wherein the sicPN comprises a detectable marker, it is contemplated that the release of the sicPN causes the detectable marker to be detected.

Thus, there remains a single stranded portion of the polynucleotide that is part of the silica shell particle. When the target polynucleotide associates with the single stranded portion of the polynucleotide that is part of the silica shell particle, it displaces and/or releases the sicPN and results in an enhanced association rate of the polynucleotide that is part of the silica shell particle with the target polynucleotide.

The association of the polynucleotide with the target polynucleotide additionally displaces and, in some aspects, releases the sicPN. The sicPN or the target polynucleotide, in various embodiments, further comprises a detectable label. Thus, in one aspect of a method wherein detection of the target polynucleotide is desired, it is the displacement and/or release of the sicPN that generates the detectable change through the action of the detectable label. In another method wherein detection of the target polynucleotide is desired, it is the target polynucleotide that generates the detectable change through its own detectable label. In methods wherein inhibition of the target polynucleotide expression is desired, it is the association of the polynucleotide that is part of the silica shell particle with the target polynucleotide that generates the inhibition of target polynucleotide expression through an antisense mechanism.

The compositions of the disclosure comprise a plurality of sicPNs, able to associate with a plurality of polynucleotides, that may be used on one or more surfaces to specifically associate with a plurality of target polynucleotides. Thus, the steps or combination of steps of the methods described below apply to one or a plurality of polynucleotides that are part of one or more silica shell particles, sicPNs and target polynucleotides.

In various aspects, the methods include use of a polynucleotide which is 100% complementary to the target polynucleotide, i.e., a perfect match, while in other aspects, the polynucleotide is at least (meaning greater than or equal to) about 95% complementary to the polynucleotide over the length of the polynucleotide, at least about 90%, at least about 85%, at least about 80%, at least about 75%, at least about 70%, at least about 65%, at least about 60%, at least about 55%, at least about 50%, at least about 45%, at least about 40%, at least about 35%, at least about 30%, at least about 25%, at least about 20% complementary to the polynucleotide over the length of the polynucleotide to the extent that the polynucleotide is able to achieve the desired of inhibition of a target gene product. It will be understood by those of skill in the art that the degree of hybridization is less significant than a resulting detection of the target polynucleotide, or a degree of inhibition of gene product expression.

Methods of Detecting a Target Polynucleotide

The disclosure provides methods of detecting a target biomolecule comprising contacting the target biomolecule with a composition as described herein. The contacting results, in various aspects, in regulation of gene expression as provided by the disclosure. In another aspect, the contacting results in a detectable change, wherein the detectable change indicates the detection of the target biomolecule. Detection of the detectable label is performed by any of the methods described herein, and the detectable label can be on a biomolecule that is part of a silica shell particle, or can be on the target biomolecule.

In some aspects, and as described above, it is the displacement and/or release of the sicPN that generates the detectable change. The detectable change is assessed through the use of a detectable label, and in one aspect, the sicPN is labeled with the detectable label. Further according the methods, the detectable label is quenched when in proximity with a surface used to template the silica shell particle. While it is understood in the art that the term "quench" or "quenching" is often associated with fluorescent markers, it is contemplated herein that the signal of any marker that is quenched when it is relatively undetectable. Thus, it is to be understood that methods exemplified throughout this description that employ fluorescent markers are provided only as single embodiments of the methods contemplated, and that any marker which can be quenched can be substituted for the exemplary fluorescent marker.

The sicPN is thus associated with the silica shell particle in such a way that the detectable label is in proximity to the surface to quench its detection. When the polynucleotide that is part of the silica shell particle comes in contact and associates with the target polynucleotide, it causes displacement and/or release of the sicPN. The release of the sicPN thus increases the distance between the detectable label present on the sicPN and the surface to which the polynucleotide was templated. This increase in distance allows detection of the previously quenched detectable label, and indicates the presence of the target polynucleotide.

Thus, in one embodiment a method is provided in which a plurality of polynucleotides are used to produce a silica shell particle by a method described herein. The polynucleotides are designed to be able to hybridize to one or more target polynucleotides under stringent conditions. Hybridization can be performed under different stringency conditions known in the art and as discussed herein. Following production of a silica shell particle with the plurality of polynucleotides, a plurality of sicPNs optionally comprising a detectable label is added and allowed to hybridize with the polynucleotides that are part of the silica shell particle. In some aspects, the plurality of polynucleotides and the sicPNs are first hybridized to each other, and then duplexes used to produce the silica shell particle. Regardless of the order in which the plurality of polynucleotide is hybridized to the plurality of sicPNs and the duplex is used to produce the silica shell particle, the next step is to contact the silica shell particle with a target polynucleotide. The target polynucleotide can, in various aspects, be in a solution, or it can be inside a cell. It will be understood that in some aspects, the solution is being tested for the presence or absence of the target polynucleotide while in other aspects, the solution is being tested for the relative amount of the target polynucleotide.

After contacting the duplex with the target polynucleotide, the target polynucleotide will displace and/or release the sicPN as a result of its hybridization with the polynucleotide that is part of the silica shell particle. The displacement and release of the sicPN allows an increase in distance between the surface and the sicPN, thus resulting in the label on the sicPN being rendered detectable. The amount of label that is detected as a result of displacement and release of the sicPN is related to the amount of the target polynucleotide present in the solution. In general, an increase in the amount of detectable label correlates with an increase in the number of target polynucleotides in the solution.

In some embodiments it is desirable to detect more than one target polynucleotide in a solution. In these embodiments, more than one sicPN is used, and each sicPN comprises a unique detectable label. Accordingly, each target polynucleotide, as well as its relative amount, is individually detectable based on the detection of each unique detectable label.

In some embodiments, the compositions of the disclosure are useful in nano-flare technology. The nano-flare has been previously described in the context of polynucleotide-functionalized nanoparticles that can take advantage of a sicPN architecture for fluorescent detection of biomolecule levels inside a living cell (described in WO 2008/098248, incorporated by reference herein in its entirety). In this system the sicPN acts as the "flare" and is detectably labeled and displaced or released from the surface by an incoming target polynucleotide. It is thus contemplated that the nano-flare technology is useful in the context of the silica shell particle described herein.

In further aspects, the silica shell particle is used to detect the presence or amount of cysteine in a sample, comprising providing a first mixture comprising a complex comprising $Hg^{2+}$ and a population of silica shell particle, wherein the population comprises silica shell particles comprising one of a pair of single stranded polynucleotides and silica shell particles comprising the other single stranded polynucleotide of the pair, wherein the pair forms a double stranded duplex under appropriate conditions having at least one nucleotide mismatch, contacting the first mixture with a sample suspected of having cysteine to form a second mixture, and detecting the melting point of the double stranded duplex in the second mixture, wherein the melting point is indicative of the presence or amount of cysteine in the sample. In some aspects, the nucleotide mismatch is an internal nucleotide mismatch. In a further aspect, the mismatch is a T-T mismatch. In still a further aspect, the sample comprising cysteine has a melting point at least about 5° C. lower than a sample without cysteine.

Methods of Inhibiting Gene Expression

Additional methods provided by the disclosure include methods of inhibiting expression of a gene product expressed from a target polynucleotide comprising contacting the target polynucleotide with a composition as described herein, wherein the contacting is sufficient to inhibit expression of the gene product. Inhibition of the gene product results from the hybridization of a target polynucleotide with a composition of the disclosure.

It is understood in the art that the sequence of a polynucleotide that is part of a silica shell particle need not be 100% complementary to that of its target polynucleotide in order to specifically hybridize to the target polynucleotide. Moreover, a polynucleotide that is part of a silica shell particle may hybridize to a target polynucleotide over one or more segments such that intervening or adjacent segments are not involved in the hybridization event (for example and without limitation, a loop structure or hairpin structure). The percent complementarity is determined over the length of the polynucleotide that is part of the silica shell particle. For example, given a silica shell particle comprising a polynucleotide in which 18 of 20 nucleotides of the polynucleotide are complementary to a 20 nucleotide region in a target polynucleotide of 100 nucleotides total length, the polynucleotide that is part of the silica shell particle would be 90 percent complementary. In this example, the remaining noncomplementary nucleotides may be clustered or interspersed with complementary nucleotides and need not be contiguous to each other or to complementary nucleotides. Percent complementarity of a polynucleotide that is part of a silica shell particle with a region of a target polynucleotide can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656).

Methods for inhibiting gene product expression provided include those wherein expression of the target gene product is inhibited by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or 100% compared to gene product expression in the absence of a nanoconjugate comprising a biomolecule and/or non-biomolecule. In other words, methods provided embrace those which results in essentially any degree of inhibition of expression of a target gene product.

The degree of inhibition is determined in vivo from a body fluid sample or from a biopsy sample or by imaging techniques well known in the art. Alternatively, the degree of inhibition is determined in vitro in a cell culture assay, generally as a predictable measure of a degree of inhibition that can be expected in vivo resulting from use of a composition as described herein. It is contemplated by the disclosure that the inhibition of a target polynucleotide is used to assess the effects of the inhibition on a given cell. By way of non-limiting examples, one can study the effect of the inhibition of a gene product wherein the gene product is part of a signal transduction pathway. Alternatively, one can study the inhibition of a gene product wherein the gene product is hypothesized to be involved in an apoptotic pathway.

It will be understood that any of the methods described herein can be used in combination to achieve a desired result. For example and without limitation, methods described herein can be combined to allow one to both detect a target polynucleotide as well as regulate its expression. In some embodiments, this combination can be used to quantitate the inhibition of target polynucleotide expression over time either in vitro or in vivo. The quantitation over time is achieved, in one aspect, by removing cells from a culture at specified time points and assessing the relative level of expression of a target polynucleotide at each time point. A decrease in the amount of target polynucleotide as assessed, in one aspect, through visualization of a detectable label, over time indicates the rate of inhibition of the target polynucleotide.

Thus, determining the effectiveness of a given polynucleotide to hybridize to and inhibit the expression of a target polynucleotide, as well as determining the effect of inhibition of a given polynucleotide on a cell, are aspects that are contemplated.

Imaging Methods

The silica shell particles disclosed herein can include a contrast agent and can be used in MRI methods. In certain embodiments, the MRI contrast agent conjugated to a polynucleotide is iron or paramagnetic radiotracers and/or complexes, including but not limited to gadolinium, xenon, iron oxide, and copper.

Methods are provided wherein presence of a composition of the disclosure is detected by an observable change. In one aspect, presence of the composition gives rise to a color change which is observed with a device capable of detecting a specific marker as disclosed herein. For example and without limitation, a fluorescence microscope can detect the presence of a fluorophore that is conjugated to a polynucleotide, which is part of a silica shell particle.

Complex Visualization Through Catalytic Metal Deposition

Methods described herein include depositing a metal on a complex formed between a silica shell particle as defined herein and a target molecule to enhance detection of the complex. Metal is deposited on the nanoparticle/target molecule when the nanoparticle/target molecule complex is contacted with a metal enhancing solution under conditions that cause a layer of the metal to deposit on the complex. Thus, the present disclosure also provides a composition comprising a silica shell particle, the silica shell particle having a single catalytic metal deposit, the composition having an average diameter of at least about 250 nanometers. In some embodiments, the average diameter is from about 250 nanometers to about 5000 nanometers. In some aspects, more than one catalytic metal deposit is contemplated.

A metal enhancing solution, as used herein, is a solution that is contacted with a silica shell particle-target molecule complex to deposit a metal on the complex. In various aspects and depending on the type of metal being deposited, the metal enhancing solution comprises, for example and without limitation, $HAuCl_4$, silver nitrate, $NH_2OH$ and hydroquinone.

In some embodiments, the target molecule is immobilized on a support when it is contacted with the silica shell particle. A support, as used herein, includes but is not limited to a column, a membrane, or a glass or plastic surface. A glass surface support includes but is not limited to a bead or a slide. Plastic surfaces contemplated by the present disclosure include but are not limited to slides, and microtiter plates. Microarrays are additional supports contemplated by the present disclosure, and are typically either glass, silicon-based or a polymer. Microarrays are known to those of ordinary skill in the art and comprise target molecules arranged on the support in addressable locations. Microarrays can be purchased from, for example and without limitation, Affymetrix, Inc.

In some embodiments, the target molecule is in a solution. In this type of assay, a silica shell particle is contacted with the target molecule in a solution to form a nanoparticle/target molecule complex that is then detected following deposition of a metal on the complex. Methods of this type are useful whether the target molecule is in a solution or in a body fluid. For example and without limitation, a solution as used herein means a buffered solution, water, or an organic solution. Body fluids include without limitation blood (serum or plasma), lymphatic fluid, cerebrospinal fluid, semen, urine, synovial fluid, tears, mucous, and saliva and can be obtained by methods routine to those skilled in the art.

The disclosure also contemplates the use of the compositions and methods described herein for detecting a metal ion (for example and without limitation, mercuric ion ($Hg^{2+}$)). In these aspects, the method takes advantage of the cooperative binding and catalytic properties of the silica shell particles comprising a DNA polynucleotide and the selective binding of a thymine-thymine mismatch for $Hg^{2+}$ (Lee et al., *Anal. Chem.* 80: 6805-6808 (2008)).

Methods described herein are also contemplated for use in combination with the biobarcode assay. The biobarcode assay is generally described in U.S. Pat. Nos. 6,974,669 and 7,323,309, each of which is incorporated herein by reference in its entirety.

Methods of the disclosure include those wherein silver or gold or combinations thereof are deposited on a silica shell particle in a complex with a target molecule.

In one embodiment, methods of silver deposition on a silica shell particle as described herein yield a limit of detection of a target molecule of about 3 pM after a single silver deposition. In another aspect, a second silver deposition improves the limit of detection to about 30 fM. Thus, the number of depositions of silver relates to the limit of detection of a target molecule. Accordingly, one of ordinary skill in the art will understand that the methods of the present disclosure may be tailored to correlate with a given concentration of target molecule. For example and without limitation, for a target molecule concentration of 30 fM, two silver depositions can be used. Concentrations of target molecule suitable for detection by silver deposition are about 3 pM, about 2 pM, about 1 pM, about 0.5 pM, about 400 fM, about 300 fM, about 200 fM, about 100 fM or less.

In methods provided, a silica shell particle is contacted with a sample comprising a first molecule under conditions that allow complex formation between the silica shell particle and the first molecule.

Methods are also provided wherein a second molecule is contacted with the first molecule under conditions that allow complex formation prior to the contacting of the silica shell particle with the first molecule.

Method are also contemplated wherein a target molecule is attached to a second silica shell particle that associates with the first silica shell particle. In some aspects, the second silica shell particle is immobilized on a solid support. In other aspects, the second silica shell particle is in a solution.

Methods provided also generally contemplate contacting a composition comprising a silica shell particle with more than one target molecules. Accordingly, in some aspects it is contemplated that a silica shell particle comprising more than one polypeptide and/or polynucleotide, is able to simultaneously recognize and associate with more than one target molecule.

In further embodiments, a target polynucleotide is identified using a "sandwich" protocol for high-throughput detection and identification. For example and without limitation, a polynucleotide that recognizes and selectively associates with the target polynucleotide is immobilized on a solid support. The sample comprising the target polynucleotide is contacted with the solid support comprising the polynucleotide, thus allowing an association to occur. Following removal of non-specific interactions, a composition comprising a silica shell particle as described herein is added. In these aspects, the silica shell particle comprises a molecule that selectively associates with the target polynucleotide, thus generating the "sandwich" of polynucleotide-target polynucleotide-silica shell particle. This complex is then exposed to a metal deposition process as described herein, resulting in highly sensitive detection. Quantification of the interaction allows for determinations relating but not limited to disease progression, therapeutic effectiveness, disease identification, and disease susceptibility.

Additional description of catalytic deposition of metal on a complex formed between a silica shell particle as defined herein and a target molecule to enhance detection of the complex is found in U.S. application Ser. No. 12/770,488, which is incorporated by reference herein in its entirety.

Detecting Modulation of Transcription of a Target Polynucleotide

Methods provided by the disclosure include a method of detecting modulation of transcription of a target polynucleotide comprising administering a silica shell particle and a transcriptional regulator and measuring a detectable change, wherein the transcriptional regulator increases or decreases transcription of the target polynucleotide in a target cell relative to a transcription level in the absence of the transcriptional regulator.

The disclosure also contemplates methods to identify the target polynucleotide. In some aspects of these methods, a library of polynucleotides is screened for its ability to detect the increase or decrease in transcription of the target polynucleotide. The library, in various aspects, is a polynucleotide library. In some aspects of these methods, a double stranded polynucleotide comprising a known sequence is used to produce a silica shell particle, creating a first silica shell particle. In some aspects, one strand of the double stranded polynucleotide further comprises a detectable marker that is quenched while the two strands of the polynucleotide remain hybridized to each other. The silica shell particle is then contacted with a target cell concurrently with a transcriptional regulator. If the polynucleotide of known sequence that is used to produce the silica shell particle hybridizes with the target polynucleotide, it results in a detectable change. The detectable change, in some aspects, is fluorescence. Observation of a detectable change that is significantly different from the detectable change observed by contacting the target cell with a second silica shell particle in which the polynucleotide comprises a different sequence than the first silica shell particle is indicative of identifying the target polynucleotide. Thus, in further aspects, each silica shell particle comprises a polynucleotide of known sequence, and in still further aspects, an increase or decrease in the detectable change when the transcriptional regulator is administered relative to the detectable change measured when a different nanoparticle comprising a polynucleotide within the library is administered is indicative of identifying the target polynucleotide. Accordingly, in some aspects the methods provide for the identification of a mRNA that is regulated by a given transcriptional regulator. In various aspects, the mRNA is increased, and in some aspects the mRNA is decreased.

Local delivery of a composition comprising a silica shell particle to a human is contemplated in some aspects of the disclosure. Local delivery involves the use of an embolic agent in combination with interventional radiology and a composition of the disclosure.

Use of a Silica Shell Particle as a Probe

The silica shell particles are, in one aspect, used as probes in diagnostic assays for detecting nucleic acids.

Some embodiments of the method of detecting a target nucleic acid utilize a substrate. Any substrate can be used which allows observation of the detectable change. Suitable substrates include transparent solid surfaces (e.g., glass, quartz, plastics and other polymers), opaque solid surface (e.g., white solid surfaces, such as TLC silica plates, filter paper, glass fiber filters, cellulose nitrate membranes, nylon membranes), and conducting solid surfaces (e.g., indium-tin-oxide (ITO)). The substrate can be any shape or thickness, but generally will be flat and thin. Preferred are transparent substrates such as glass (e.g., glass slides) or plastics (e.g., wells of microtiter plates). Methods of attaching polynucleotides to a substrate and uses thereof with respect to silica shell particles are disclosed in U.S. Patent Application 20020172953, incorporated herein by reference in its entirety.

By employing a substrate, the detectable change can be amplified and the sensitivity of the assay increased. In one aspect, the method comprises the steps of contacting a target polynucleotide with a substrate having a polynucleotide attached thereto, the polynucleotide (i) having a sequence complementary to a first portion of the sequence of the target nucleic acid, the contacting step performed under conditions effective to allow hybridization of the polynucleotide on the substrate with the target nucleic acid, and (ii) contacting the target nucleic acid bound to the substrate with a first type of silica shell particle having a polynucleotide attached thereto, the polynucleotide having a sequence complementary to a second portion of the sequence of the target nucleic acid, the contacting step performed under conditions effective to allow hybridization of the polynucleotide that is part of the silica shell particle with the target nucleic acid. Next, the first type of silica shell particle bound to the substrate is contacted with a second type of silica shell particle comprising a polynucleotide, the polynucleotide on the second type of silica shell particle having a sequence complementary to at least a portion of the sequence of the polynucleotide used to produce the first type of silica shell particle, the contacting step taking place under conditions effective to allow hybridization of the polynucleotides on the first and second types of silica shell particles. Finally, a detectable change produced by these hybridizations is observed.

The detectable change that occurs upon hybridization of the polynucleotides on the silica shell particles to the nucleic acid may be a color change, the formation of aggregates of the silica shell particles, or the precipitation of the aggregated silica shell particles. The color changes can be observed with the naked eye or spectroscopically. The formation of aggregates of the silica shell particles can be observed by electron microscopy or by nephelometry. The precipitation of the aggregated silica shell particles can be observed with the naked eye or microscopically. Preferred are changes observable with the naked eye. Particularly preferred is a color change observable with the naked eye.

The methods of detecting target nucleic acid hybridization based on observing a color change with the naked eye are cheap, fast, simple, robust (the reagents are stable), do not require specialized or expensive equipment, and little or no instrumentation is required. These advantages make them particularly suitable for use in, e.g., research and analytical laboratories in DNA sequencing, in the field to detect the presence of specific pathogens, in the doctor's office for quick identification of an infection to assist in prescribing a drug for treatment, and in homes and health centers for inexpensive first-line screening.

A silica shell particle comprising a polynucleotide can be used in an assay to target a target molecule of interest. Thus, the silica shell particle comprising a polynucleotide can be used in an assay such as a bio barcode assay. See, e.g., U.S. Pat. Nos. 6,361,944; 6,417,340; 6,495,324; 6,506,564; 6,582, 921; 6,602,669; 6,610,491; 6,678,548; 6,677,122; 6682,895; 6,709,825; 6,720,147; 6,720,411; 6,750,016; 6,759,199; 6,767,702; 6,773,884; 6,777,186; 6,812,334; 6,818,753; 6,828,432; 6,827,979; 6,861,221; and 6,878,814, the disclosures of which are incorporated herein by reference.

EXAMPLES

Materials and Methods

Experimental Details: Materials were purchased from Sigma-Aldrich Co. and used without further purification. SH—$(CH_2)_{11}$-$(EG)_6$-$OCH_2$—COOH was purchased from Prochimia (Prochimia, Poland). The cross-linker p-maleimidophenyl isocyanate (PMPI) was purchased from Thermo Scientific (Rockford, Ill.). STEM characterization was conducted on a Hitachi HD-2300A STEM microscope (Hitachi High-Tech Co., Japan). DLS data were acquired from a MALVERN Zetasizer, Nano-ZS (Malvern Instruments, UK). UV-Vis data were obtained on a Cary 5000 UV-Vis-NIR spectrophotometer (Varian Inc., CA, USA).

Synthesis of Au@$SiO_2$ Particles: 13 nm citrate-stabilized Au NPs were synthesized according to literature methods (Frens, G. *Nature, Phys. Sci.* 1973, 241, 20-22). Briefly, 1.67 mL of 0.3M $HAuCl_4$ and 497 mL Nanopure $H_2O$ were brought to a boil under reflux conditions. Next, 1.67 mL of 1.16 M sodium citrate tribasic dihydrate was added quickly and all at once. The solution was boiled for 30 minutes, cooled to room temperature, and filtered with a 45 μm Milipore circular filter under vacuum. The Au NPs were then passivated with SH—$(CH_2)_{11}$-$(EG)_6$-$OCH_2$—COOH (~1.25 μL per 25 mL Au NPs) and shaken overnight. The particles were spun down and resuspended in a 50/50 (v/v) water/ethanol mixture. The particles were spun down a second time and resuspended in ethanol.

To synthesize the Au@$SiO_2$ particles, 22.5 mL of 2.45 nM Au NPs in ethanol (for 13 nm Au NP, $\in$=2.7E8 M-1 cm-1) were placed in a 50 mL Falcon tube. Then, 225 μL Nanopure $H_2O$, 900 μL ammonium hydroxide (30% in water), and 135 μL tetraethyl orthosilicate (TEOS) (20× diluted from stock) were added in sequence. It is important to note that the TEOS is extremely air sensitive; a new bottle was opened for each experiment. The particles were then vigorously shaken for 8 hours. To purify the Au@$SiO_2$ particles, they were spun down and resuspended in ethanol 3 times. The particles were then heated at 60° C. for 24 hours under gentle shaking to ensure homogeneous silica shells.

DNA Functionalization Procedure: Oligonucleotides were synthesized on a MM48 Synthesizer (Bioautomation) using standard solid-phase phosphoramidite chemistry. Bases and reagents were purchased from Glen Research Co. Oligonucleotides were purified by reverse-phase high performance liquid chromatography (HPLC, Varian). The DNA sequences used for experiments are listed below.

```
                                            (SEQ ID NO: 1)
Anti-eGFP Sequence:
3'-HS(C3H6)-AAAAAAAAAAGGTGTTCAAGTCGCACAGGC-5'

(SEQ ID NO: 2)
Scramble Sequence:
3'HS(C3H6)-AAAAAAAAAATTATAACTATTCCTA-5'

(SEQ ID NO: 3)
Cy5-labeled anti-eGFP Sequence
(for cell imaging):
3'HS(C3H6)-AAAAAAAAAAGGTG-TTCAAGTCGCACAGGC- Cy5-5'

(SEQ ID NO: 4)
Sequence for melting analysis:
3'HS(C3H6)-AAAAAAAAAAAGACGAATATTAATAAG5'

(SEQ ID NO: 5)
Self-complementary linker for melting
analysis:
3'-CGCGATTTTTTTTTTTTAGTCACG-

ACGAGTCATTTTTTTTTTTATTCTTAAATATTCGTCTT-5'
```

The Au@$SiO_2$ particles were resuspended in dry toluene, excess (aminopropyl)triethoxysilane (APTES) was added, and the solution was shaken vigorously for 1 h. The particles were then washed twice with dry toluene and once with dry acetonitrile. 150 mg PMPI were added to the Au@SiO$_2$ NPs in acetonitrile and shaken vigorously overnight. The particles were then washed twice with dry acetonitrile and once with Nanopure H$_2$O. The disulfide-terminated oligonucleotides were cleaved with dithiolthreitol (DTT) (0.1M, 1 h) and purified on size exclusion columns (SEPHADEX™ G-25 DNA Grade, GE Healthcare). The purified oligonucleotides were then added to the Au@SiO$_2$ NPs in water and slowly salted to 0.3 M NaCl over ~4 h. 0.01 (wt %) SDS was added to prevent the particles from sticking to the containers. The final mixture was shaken for ~24 h to complete the oligonucleotide functionalization process. The particles were centrifuged three times and resuspended in sterile phosphate buffered saline (PBS) for cell studies. To prepare the hollow SiO$_2$ particles, I$_2$ was added to the DNA-functionalized Au@SiO$_2$ NPs and shaken for 1 h at ~50° C. The particles were then dialyzed overnight against water (Slide-A-Lyzer® Dialysis Cassette, 10,000 MWCO, Thermo Scientific) to remove any excess I$_2$.

Quantification of Oligonucleotides/Particle: Quantification of the number of DNA oligonucleotides per nanoparticle was accomplished through use of the Quant-iT™ OliGreen® ssDNA Kit (INVITROGEN™). DNA functionalized Au@SiO$_2$ nanoparticles (2 nM) were first treated with I$_2$ to dissolve the gold core. 100 μL of 1× OliGreen® dye solution was added to each sample in triplicate, mixed, and allowed to incubate at room temperature for five minutes. The OliGreen® fluorescence was measured using a BioTek® Synergy Microplate Reader with excitation wavelength=480 nm and emission wavelength=520 nm. The oligonucleotide concentration was quantified by comparison with a standard curve constructed from unconjugated DNA oligonucleotides treated with the OliGreen® dye.

Cell Culture and Imaging: C166 cells were purchased from American Tissue Culture Collection (ATCC) and were grown in 5% CO$_2$ at 37° C. in Dulbecco's modified Eagle's medium (DMEM) supplemented with 10% heat-inactivated fetal bovine serum. 24 hours prior to particle treatment, cells were plated on 35 mm FluoroDish (World Precision Instruments). On the day of transfection, the Au@SiO$_2$ and hollow SiO$_2$ SNAs were diluted in 0.5 mL cell culture media and added to each well at a final Au NP concentration of 5 nM. After overnight incubation, cells were fixed by 1% formaldehyde (Santa Cruz Biotechnology) in PBS followed by three washes with PBS. The fixed cells were then imaged with a Zeiss LSM 510 inverted laser scanning confocal microscope at 60× magnification. Fluorescence excitation for Cy5 was set at 633 nm and the emission was collected at 650-710 nm. In the Z-stack mode, images of planes were collected step-wise and the depth between each stack was set to be 0.5 μm.

GFP Knockdown Analysis by qRT-PCR: Gene regulation functionality of SNAs was assayed by quantitative real-time reverse-transcriptase polymerase chain reaction. After overnight incubation with the Au@SiO$_2$ and hollow SiO$_2$ SNAs, C166 cells cultured in 12-well plates (Corning®) were harvested and the total RNA was extracted from each well of cells with the RNeasy® Mini Kit (Qiagen®). Extracted RNA was then mixed with LightCycler@ RNA Master SYBR Green 1 (Roche) reagents according to standard protocols from the manufacturer. One-step qRT-PCR was performed on a LightCycler® 480 system (Roche) and the resulting C$_t$ values were used to quantify the relative eGFP gene knockdown. The relative abundance of eGFP mRNA was normalized to the ApoB gene expression and the standard deviation for this data was calculated from three independent experiments. The PCR primers used in this experiment were: eGFP forward (5'-CCA CAT GAA GCA GCA CGA CTT-3'; SEQ ID NO: 6), GFP reverse (5'-GGT GCG CTC CTG GAC GTA-3', SEQ ID NO: 7), ApoB forward (5'-CAC GTG GGC TCC AGC ATT-3', SEQ ID NO: 8) and ApoB reverse (5'-TCA CCA GTC ATT TCT GCC TTT G-3', SEQ ID NO: 9).

Cell Toxicity Assay: The cytotoxicity of the Au@SiO$_2$ and hollow SiO$_2$ SNAs was evaluated by the 3-(4,5-dimethylthiazol-2-yl)-2,5 diphenyltetrazolium bromide (MTT) assay. Briefly, C166 cells were seeded on a 96 well plate in 100 μL of media and incubated for 24 h. The cells were then treated with particles at the final Au NP concentration of 5 nM. Cells without treatment were used as a control. After 24 h incubation, the medium was removed, the cells were washed three times with PBS and then incubated with 100 μL fresh culture medium in addition to 10 μL of freshly-made 12 mM MTT solution at 37° C. in 5% CO$_2$ for 4 h. Then 100 μL lysis buffer (20 g SDS dissolved in 50 mL H$_2$O and supplemented with 50 mL N,N-Dimethylformamide, pH 4.7) was added to each well. Cells were further incubated overnight and the absorbance was measured at 620 nm using a BioTek® Synergy HT multi-detection microplate plate reader. Each condition was repeated in triplicate in three independent experiments.

REFERENCES (1) Rosi, N. L.; Giljohann, D. A.; Thaxton, C. S.; Lytton-Jean, A. K. R.; Han, M. S.; Mirkin, C. A. *Science* 2006, 312, 1027-1030.
(2) Cutler, J. I.; Auyeung, E.; Mirkin, C. A. *J. Am. Chem. Soc.* 2012, 134, 1376-1391.
(3) Sokolova, V.; Epple, M. *Angew. Chem., Int. Ed.* 2008, 47, 1382-1395.
(4) Lv, H.; Zhang, S.; Wang, B.; Cui, S.; Yan, J. J. *Controlled Release* 2006, 114, 100-109.
(5) Dokka, S.; Toledo, D.; Shi, X.; Castranova, V.; Rojanasakul, Y. *Pharm. Res.* 2000, 17, 521-525.
(6) Soenen, S. J. H.; Brisson, A. R.; De Cuyper, M. *Biomaterials* 2009, 30, 3691-3701.
(7) Seferos, D. S.; Giljohann, D. A.; Hill, H. D.; Prigodich, A. E.; Mirkin, C. A. *J. Am. Chem. Soc.* 2007, 129, 15477-15479.
(8) Patel, P. C.; Giljohann, D. A.; Daniel, W. L.; Zheng, D.; Prigodich, A. E.; Mirkin, C. A. *Bioconjugate Chem.* 2010, 21, 2250-2256.
(9) Giljohann, D. A.; Seferos, D. S.; Patel, P. C.; Millstone, J. E.; Rosi, N. L.; Mirkin, C. A. *Nano Lett.* 2007, 7, 3818-3821.
(10) Lytton-Jean, A. K. R.; Mirkin, C. A. *J. Am. Chem. Soc.* 2005, 127, 12754-12755.
(11) Seferos, D. S.; Prigodich, A. E.; Giljohann, D. A.; Patel, P. C.; Mirkin, C. A. *Nano Lett.* 2009, 9, 308-311.
(12) Massich, M. D.; Giljohann, D. A.; Seferos, D. S.; Ludlow, L. E.; Horvath, C. M.; Mirkin, C. A. *Mol. Pharmaceutics.* 2009, 6, 1934-1940.
(13) Cutler, J. I.; Zhang, K.; Zheng, D.; Auyeung, E.; Prigodich, A. E.; Mirkin, C. A. *J. Am. Chem. Soc.* 2011, 133, 9254-9257.
(14) Bhabra, G.; Sood, A.; Fisher, B.; Cartwright, L.; Saunders, M.; Evans, W. H.; Surprenant, A.; Lopez-Castejon, G.; Mann, S.; Davis, S. A.; Hails, L. A.; Ingham, E.; Verkade, P.; Lane, J.; Heesom, K.; Newson, R.; Case, C. P. *Nat. Nanotechnol.* 2009, 4, 876-883.
(15) Nel, A.; Xia, T.; Maedler, L.; Li, N. *Science* 2006, 311, 622-627.
(16) Chompoosor, A.; Saha, K.; Ghosh, P. S.; Macarthy, D. J.; Miranda, O. R.; Zhu, Z.-J.; Arcaro, K. F.; Rotello, V. M. *Small* 2010, 6, 2246-2249.

(17) Letsinger, R. L.; Elghanian, R.; Viswanadham, G.; Mirkin, C. A. *Bioconjugate Chem.* 2000, 11, 289-291.
(18) Park, J.-H.; Gu, L.; von Maltzahn, G.; Ruoslahti, E.; Bhatia, S, N.; Sailor, M. J. *Nat. Mater.* 2009, 8, 331-336.
(19) Yamada, H.; Urata, C.; Aoyama, Y.; Osada, S.; Yamauchi, Y.; Kuroda, K. *Chem. Mater.* 2012, 24, 1462-1471.
(20) Frens, G. *Nat. Phys. Sci.* 1973, 241, 20-22.
(21) Marinakos, S. M.; Novak, J. P.; Brousseau, L. C., III; House, A. B.; Edeki, E. M.; Feldhaus, J. C.; Feldheim, D. L. *J. Am. Chem. Soc.* 1999, 121, 8518-8522.
(22) Lu, Y.; Yin, Y.; Li, Z.-Y.; Xia, Y. *Nano Lett.* 2002, 2, 785-788.
(23) Mine, E.; Yamada, A.; Kobayashi, Y.; Konno, M.; Liz-Marzan, L. M. *J. Colloid Interface Sci.* 2003, 264, 385-390.
(24) Wong, Y. J.; Zhu, L.; Teo, W. S.; Tan, Y. W.; Yang, Y.; Wang, C.; Chen, H. *J. Am. Chem. Soc.* 2011, 133, 11422-11425.
(25) Jin, L.; Horgan, A.; Levicky, R. *Langmuir* 2003, 19, 6968-6975.
(26) Barnes, C. A.; Elsaesser, A.; Arkusz, J.; Smok, A.; Palus, J.; Lesniak, A.; Salvati, A.; Hanrahan, J. P.; de Jong, W. H.; Dziubaltowska, E.; Stepnik, M.; Rydzynski, K.; McKerr, G.; Lynch, I.; Dawson, K. A.; Howard, C. V. *Nano Lett.* 2008, 8, 3069-3074.
(27) Xue, C.; Chen, X.; Hurst, S. J.; Mirkin, C. A. *Adv. Mater.* 2007, 19, 4071-4074.
(28) Banholzer, M. J.; Harris, N.; Millstone, J. E.; Schatz, G. C.; Mirkin, C. A. *J. Phys. Chem. C* 2010, 114, 7521-7526.
(29) Kelly, K. L.; Coronado, E.; Zhao, L. L.; Schatz, G. C. *J. Phys. Chem. B* 2003, 107, 668-677.
(30) Jin, R.; Wu, G.; Li, Z.; Mirkin, C. A.; Schatz, G. C. *J. Am. Chem. Soc.* 2003, 125, 1643-1654.
(31) Hermanson, G. T. *Bioconjugate Techniques,* 2nd ed.; Academic Press: San Diego, Calif., 2008.
(32) Kolb, H. C.; Finn, M. G.; Sharpless, K. B. *Angew. Chem., Int. Ed.* 2001, 40, 2004-2021.
(33) Baskin, J. M.; Prescher, J. A.; Laughlin, S. T.; Agard, N. J.; Chang, P. V.; Miller, I. A.; Lo, A.; Codelli, J. A.; Bertozzi, C. R. *Proc. Natl. Acad. Sci. U.S.A.* 2007, 104, 16793-16797.
(34) Liu, S.; Han, M. *Adv. Funct. Mater.* 2005, 15, 961-967.

What is claimed:

1. A method comprising
   a) admixing a nanoparticle and a silica reagent to form a silica shell nanoparticle;
   b) admixing the silica shell nanoparticle and a biomolecule to attach the biomolecule to at least a portion of the silica shell nanoparticle surface; and
   c) at least partially removing the nanoparticle to form a biomolecule-surface modified silica shell particle.

2. The method of claim 1, wherein the nanoparticle is metallic.

3. The method of claim 1, wherein the silica reagent comprises a silicate.

4. The method of claim 3, wherein the silicate comprises tetraethyl ortho silicate (TEOS).

5. The method of claim 1, wherein the biomolecule is a polynucleotide, peptide, polypeptide, phospholipid, oligosaccharide, therapeutic agent or mixtures thereof.

6. The method of claim 5, wherein the biomolecule comprises a polynucleotide conjugated to a contrast agent.

7. The method of claim 1, further comprising activating the silica shell nanoparticle with a reagent to introduce a thiol reactive moiety on at least a portion of the silica shell nanoparticle surface.

8. The method of claim 1, wherein the biomolecule comprises a thiol at one end.

9. The method of claim 1, wherein density of the biomolecules on the surface is at least 2 pmol/cm$^2$.

10. The method of claim 1, wherein the nanoparticle is fully removed and the silica shell particle is a hollow particle.

11. The method of claim 1, wherein the removing comprises contacting the silica shell nanoparticle with a nanoparticle dissolving agent.

12. The method of claim 11, wherein the nanoparticle dissolving agent comprises iodine or potassium cyanide.

13. The method of claim 1, the nanoparticle has a diameter of about 5 nm to about 500 nm.

14. The method of claim 1, wherein the silica shell nanoparticle has a diameter of about 30 nm to about 500 nm.

15. The method of claim 1, wherein the silica shell has a thickness of about 20 nm to about 200 nm.

16. The method of claim 1, further comprising admixing the silica shell particle with a therapeutic agent to form a payload particle.

17. The method of claim 16, wherein the therapeutic agent comprises a protein, a peptide, an antibody, an oligonuceltoide, a polynucleotide, or a drug.

18. A silica shell particle prepared by the method of claim 1.

* * * * *